US008778889B2

(12) United States Patent
Leung

(10) Patent No.: US 8,778,889 B2
(45) Date of Patent: *Jul. 15, 2014

(54) ANTIMICROBIAL DECAPEPTIDE ORAL HYGIENE TREATMENT

(75) Inventor: Kai P. Leung, Libertyville, IL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/582,561

(22) Filed: Oct. 18, 2006

(65) Prior Publication Data
US 2007/0098651 A1 May 3, 2007

Related U.S. Application Data

(63) Continuation-in-part of application No. 10/795,514, filed on Mar. 9, 2004, now Pat. No. 7,494,980.

(60) Provisional application No. 60/455,206, filed on Mar. 10, 2003, provisional application No. 60/727,428, filed on Oct. 18, 2005, provisional application No. 60/735,915, filed on Nov. 14, 2005.

(51) Int. Cl.
C07K 7/06 (2006.01)
A61K 38/08 (2006.01)
A61K 9/68 (2006.01)
A61B 5/00 (2006.01)

(52) U.S. Cl.
USPC ............... 514/21.6; 424/48; 424/49; 424/9.7

(58) Field of Classification Search
None
See application file for complete search history.

(56) References Cited

U.S. PATENT DOCUMENTS

| | | | | |
|---|---|---|---|---|
| 3,930,026 A * | 12/1975 | Clark | | 426/3 |
| 4,476,107 A * | 10/1984 | Schmolka | | 424/49 |
| 5,145,664 A * | 9/1992 | Thompson | | 424/49 |
| 5,304,633 A * | 4/1994 | Tomita et al. | | 514/12 |
| 5,989,522 A | 11/1999 | Friedman | | |
| 6,365,130 B1 | 4/2002 | Barry | | |
| 6,365,635 B1 | 4/2002 | Nomura et al. | | |
| 6,414,035 B1 | 7/2002 | Vargas Munita et al. | | |
| 6,464,962 B2 | 10/2002 | Heckendorn et al. | | |
| 6,503,539 B2 | 1/2003 | Gestrelius et al. | | |
| 7,494,980 B2 * | 2/2009 | Leung et al. | | 514/15 |
| 2004/0091432 A1 | 5/2004 | Dulin | | |
| 2004/0224897 A1 | 11/2004 | Leung et al. | | |

FOREIGN PATENT DOCUMENTS

| | | |
|---|---|---|
| WO | 94/12150 A1 | 6/1994 |
| WO | WO 99/26971 | 6/1999 |
| WO | WO 02/45575 A2 | 6/2002 |
| WO | WO 2005/092271 A1 | 10/2005 |

OTHER PUBLICATIONS

S.Y. Hong et al. Antimicrob. Agents Chemother. (1998) 42(10), pp. 2534-2541.*
K.-P. Leung et al. J. Dent. Res. (2005) 84(12), pp. 1172-1177.*
Bateman, Andrew et al., "The Isolation and Identification of Multiple Forms of the Neutrophil Granule Peptides from human Leukemic Cells", J Biol Chem, Apr. 25, vol. 266, 1991, pp. 7524-7530.
Blondelle, Sylvie E. et al., "Novel Antimicrobial Compounds Identified Using Synthetic Combinatorial Library Technology", Trends in Biotechnology, 1996, vol. 14, pp. 60-65.
Blondelle, Sylvie E. et al., "Identification of Antimicrobial Peptides by Using Combinatorial Libraries Made Up of Unnatural Amino Acids", Antimicrobial Agents and Chemotherapy, Oct. 1994, vol. 38, No. 10, pp. 2280-2286.
Blondelle, Sylvie E. et al., "Synthetic Combinatorial Libraries: Novel Discovery Strategy for Identification of Antimicrobial Agents", Antimicrobial Agents and Chemotherapy, May 1996, vol. 40, No. 5, pp. 1067-1071.
Blondelle, Sylvie E. et al., "Rapid Identification of Compounds with enhanced Antimicrobial Activity by Using Conformationally Defined Combinatorial Libraries", Biochem. J, 1996, vol. 313, pp. 141-147.
Boggiano, Cesar, "Successful Identification of Novel Agents to Control Infectious Diseases from Screening Mixture-Based Peptide Combinatiorial Libraries in Complex Cell-Based Bioassays".
Boman, Hans G., "Antibacterial Peptides: Key Componets Needed in Immunity", Cell, Apr. 19, 1991, vol. 65, pp. 205-207.
Boman, Hans G., "Gene-Encoded Peptide Antibiotics and the Concept of Innate Immunity; An Update Review", Scand. J. Innunol., 1998, vol. 48, pp. 15-25.
Bowden, G. H. W., "Which Bacteria are Cariogenic in Humans?", Risk markers for Oral Diseases, vol. 1, Dental Caries, 1991, Cambridge University Press, Cabridge, UK, pp. 266-286.
Chen, Jie et al., "Development of Protegrins for the Treatment and Prevention of Oral Mucositis: Structure-Activity Relationships of Synthetic Protegrin Analogues", Biopolymers (Peptide Science), 2000, vol. 55, pp. 88-98.
Concannon, Sean P. et al., "Susceptibility of Oral Bacteria to an Antimicrobial Decapeptide", Journal of Medical Microbiology, 2003, vol. 52, pp. 1083-1093.
Davies, Julian, "Inactivation of Antibiotics and the Dissemination of Resistance Genes", Science, Apr. 15, 1994, vol. 264, pp. 375-381.
Decker, Thomas et al., "A Quick and Simple Method for the Quantitation of Lactate Dehydorgenase Release in Measurements of Cellular Cytotoxicity and Tumor Necrosis Factor (TNF) Activity", Journal of Immunological Method, 1988, vol. 15, pp. 61-69.
Donlan, Rodney M. et al, "Biofilms: Survival Mechanisms of Clinically Relevant Microorganims", Clinical Mirobiology Reviews, Apr. 2002, vol. 15, No. 2, pp. 167-193.

(Continued)

Primary Examiner — Satyanarayana R Gudibande
(74) Attorney, Agent, or Firm — Elizabeth Arwine; Cahn & Samuels, LLP

(57) ABSTRACT

A method for promoting oral hygiene that treats mature biofilms comprises the step of applying the antimicrobial peptide KSL and a surface active agent to the oral environment of applying KSL after mechanical disruption of the biofilm. An antiplaque chewing gum comprising KSL provides a sustained release oral hygiene treatment.

7 Claims, 15 Drawing Sheets
(5 of 15 Drawing Sheet(s) Filed in Color)

(56) References Cited

OTHER PUBLICATIONS

Dyson H. Jane et al., "Defining Solution Conformations of Small Linear Peptides", Annu. Rev. Biophys. Biophys. Chem., 1991, vol. 20, pp. 519-538.

Elsbach, Peter, "What is the Real Role of Antimicrobial Polypeptides that can Mediate Several Other Inflammatory Responses?", The Journal of Clinical Investigation, Jun. 2003, vol. 111, No. 11, pp. 1643-1645.

Friedrich, Carol et al., "Salt-Resistant Alpha-Helical Cationic Antimicrobial Peptides", Antimicrobial Agents and Chemotherapy, Jul. 1999, vol. 43, No. 7, pp. 1542-1548.

Fuchs, Peter C. et al., "In Vitro Antimicrobial Activity of MSI-78, a Magainin Analog", Antimicrobial Agents and Chemotherapy, May 1998, vol. 42, No. 5, pp. 1213-1216.

Gibbons, R. J., "Role of Adhesion in Microbial Colonization of Host Tissues: A Contribution of Oral Microbiology", J. Dent Res, 1996, vol. 3, pp. 866-870.

Guthmiller, Janet J. et al., "Susceptibilities of Oral Bacteria and Yeast to Mannalian Cathelicidins", Antimicrobial Agents and Chemotherapy, Nov. 2001, vol. 45, No. 11, pp. 3216-3219.

Hancock, Robert E. W. "Antibacterial Peptides and the Outer Membranes of Gram-Negative Bacilli", J. Med. Microbiol (Editorial), 1997, vol. 46, pp. 1-3.

Hancock, Robert E. W., "Peptide Antibiotics", The Lancet, Feb. 8, 1997, vol. 349, pp. 418-422.

Hancock, Robert E. W. et al., "Cationic Peptides: A New Source of Antibiotics", TIBTECH, Feb. 1998, vol. 16, pp. 82-88.

Hancock, Robert E. W. et al., "Peptides Antibiotics", Antimicrobial Agents and Chemotherapy, Jun. 1990, vol. 43, No. 6, pp. 1317-1323.

Hancock, Robert E. W. et al., "Role of Membranes in the Activities of Antimicrobial Cationic Peptides", FEMS Microbiology Letters 206, 2002, pp. 143-149.

Hancock, Robert E. W. et al., "Cationic Bactericidal Peptides", Advances in Microbial Physiology, 1995, vol. 37, pp. 135-175.

Helmerhorst, Eva J. et al., "Synthetic Histatin Analogues with Broad-Spectrum Antimicrobial Activity", Biochem. J., 1997, vol. 325, pp. 39-45.

Helmerhorst, Eva J. et al., "The Effects of Histatin-Derived Basic Antimicrobial Peptides on Oral Biofilms", J. Dent Res, Jun. 1999, vol. 78, No. 6, pp. 1245-1250.

Henderson et al., "Bacteria-Cytokine Interactions in Health and Disease", Portland Press, pp. 351-354.

Hong, Sung Y. et al., Identification and Characterization of Novel Antimicrobial Decapeptides Generated by Combinational Chemotherapy, Oct. 1998, vol. 42, No. 10, pp. 2534-2541.

Kaiser, E. et al., "Color Test for Detection of Free Terminal Amino Groups in the Solid-Phase Synthesis of Peptides", Short Communications, Oct. 1969, pp. 595-599.

Kilian, Mogens et al., "Taxonomic Study of Viridans Streptococci: Description of *Stretococcus gordonii* sp. Nov. and Emended Descriptions of *Streptococcus sanguis* (White and Niven 1946), *Streptococcus oralis* (Bridge and Sneath 1982), and *Streptococcus mitis* (Andrewes and Hordes 1906)", International Journal of Systematic Bacterilogy, Oct. 1989, vol. 39, No. 4, pp. 471-484.

Koczulla, Andreas R. et al., "Antimicrobial Peptides—Current Status and Therapeutic Potential", Drugs, 2003, Vo. 63, No. 4, pp. 389-406.

Koczulla, Rembert et al., "An Angiogenic Role for the Human Peptide Antibiotic LL-37/hCAP-18", The Journal of Clinical Investigation, Jun. 2003, vol. 111, No. 11, pp. 1665-1672.

Kolenbrander, Paul E., "Adhere Today, Here Tomorrow; Oral Bacterial Adherence", Journal of Bacteriology, Jun. 1993, vol. 175, No. 11, pp. 3247-3252.

Kolenbrander, Paul E., "Coaggregation: Specific Adherence Among Human Oral Plaque Bacteria", The FAEB Journal, Mar. 1993, vol. 7, pp. 406-413.

Lee, In Hee et al., "Effects of pH and Salinity on the Antimicrobial Properties of Clavanins", Infection and Immunity, Jul. 1997, vol. 65, No. 7, pp. 2898-2903.

Lisle, John T. et al., "Fluorescent Probes Applied to Physiological Charcterization of Bacterial Biolfilms", Methods in Enzymology, 1999, vol. 310, pp. 166-178.

Loesche, W. J. et al., "Bacteriology of Human Experimental Gingivitis: Effects of Plaque and Gingivitis Score", Infection and Immunity, Sep. 1978, vol. 21, pp. 830-839.

MacKay, Bruce J., et al., "Growth-Inhibitory and Bactericidal Effects of Human Parotid Salivary Histidine-Rich Polypeptides on *Streptococcus mutans*", Infection and Immunity, Jun. 1984, vol. 44, No. 3, pp. 695-701.

Marsh, P. D. et al., "Dental Plaque as Biofilm", Journal of Industrial Microbiology, 1995, vol. 15, 169-175.

Mickels, Nancy et al., "Clinical and Microbial Evaluation of a Histatin-containg Mouthrinse in Humans with Experimental Gingivitis", Journal of Clinical Periodontology, May 2001, vol. 28, No. 5, pp. 404-410.

Miyasaki, Kenneth T. et al., "Killing of Oral, Gram-Negative, Facultative Bacteria by the Rabbit Defensin, NP-1", Oral Microbiol Innunol, 1990, vol. 5, pp. 315-319.

Miyasaki, Kenneth T. et al., "Sensitivity of Periodontal Pathogens to the Bactericidal Activity of Synthetic Protegrins, Antibiotic Peptides Derived from Porcine Leukocytes", J. Dent Res, Aug. 1997, vol. 76, No. 8, pp. 1453-1459.

Miyasaki, Kenneth T. et al., "Killing of *Fusobacterium nucleatum*, *Porphyromonas gingivalis* and *Prevotella intermedia* by Protegrins", Journal of Periodontal Research, 1998, vol. 33, pp. 91-97.

Mosca, Deborah A. et al., "IB-367, A Protegin Peptide with in Vitro and in Vivo Activities Against the Microflora Associated with Oral Mucositis", Antimicrobial Agents and Chemotherapy, Jul. 2000, vol. 44, No. 7, pp. 1803-1808.

Mosmann, Tim, "Rapid Colorimetric Assay for Cellular Growth and Survival: Application to Proliferation and Cytotoxicity Assays", Journal of Immunological Methods, 1983, vol. 65, pp. 55-63.

Murakami, M. et al., "Cathelicidin Antimicrobial Peptides are Expressed in Salivary Glands and Saliva", J Dent Res, 2002, vol. 81, No. 12, pp. 845-850.

Nizet, Victor et al., "Innate Antimicrobial Peptide Protests the Skin from Invasive Bacterial Infection", Naure, Nov. 22, 2001, vol. 414, pp. 454-457.

Oh, J. E. et al., "Structure-Activity Relationship Study: Short Antimicrobial Peptides", The Journal of Peptide Reseach, Jan. 199, vol. 53, No. 1, pp. 41-46, 1999.

Pardi, A. et al., "Calibration of the Angular Dependence of the Amide Proton-Cα Proton Coupling Constants, 3 JHNα, in a Globular Protein—Use of 3 JHNα for Identification of Helical Secondary Structure", J. Mol, Biol. Jan. 1984, vol. 180, pp. 741-751.

Raj, Periathamby A. et al., "Salivary Histatin 5: Dependence of Sequence, Chain Length, and Helical Conformation for Candidacidal Activity", The Journal of Biological Chemistry, Mar. 5, 1990, vol. 265, No. 7, pp. 3898-3905.

Raj, Periathamby A. et al., "Delineation of an Active Fragment and Poly(L-proline) II Conformation for Candidacidal Activity of Bactenecin 5", Biochemistry, 1996, vol. 35, pp. 4314-4325.

Raj, Periathamby A. et al., "Structure of Human Salivary Histatin 5 in Aqueous and Nonaqueous Solutions", Biopolymers, 1998, vol. 45, pp. 51-67.

Raj, Periathamby A. et al., "Synthesis, Microbicidal Activity, and Solution Structure of the Dodecapeptide from Bovine Neutrophils", Biopolymers, 2000, vol. 53, pp. 281-292.

Raj, Periathamby A. et al., "Large-scale Synthsis and Functional Elements for the Antimicrobial Activity of Defensins", Biochem. J., 2000, vol. 347, pp. 633-641.

Rothstein, David M. et al., "Anticandida Activity Is Retained in P-113, a 12-Amino-Acid Fragment of Histatin 5", Antimicrobial Agents and Chemotherapy, May 2001, vol. 45, No. 5, pp. 1367-1375.

Schutze, G. E. et al., "Resistant Pneumococcus: A Worldwide Problem", Infection, 1994, vol. 22, No. 4, pp. 233-237.

Slots, J. et al., "The Occurrence of *Actinobacillus actinomycetemcomitans*, *Bacteroides gingivalis* and *Bacteroides intermedius* in Destructive Periodontal Disease in Adults", Journal of Clinical Periodontology, 1986, vol. 13, pp. 570-577.

(56) References Cited

OTHER PUBLICATIONS

Socransky, S. S. et al., "Microbial Complexes in Subgingival Plaque", Journal of Clinical Periodontology, 1998, vol. 25, pp. 134-144.

Sumney, David L. et al., "Charatcterization of Bacteria Isolated from Human Root Surface Carious Lesions", J Dent Res, Mar.-Apr. 1974, vol. 53, No. 2, pp. 343-351.

Tamamura, Hirokazu et al., "Synthesis of Protegrin-Related Peptides and Their Antibacterial and Anti-human Immunodeficiency Virus Activity", Chem. Pharm. Bull. 1995, Vo. 43, No. 5, pp. 853-858.

Tanaka, D. et al., "Sensitivity of *Actinobacillus actinomycetemcomitans* and *Capnocytophaga* spp. To the Bactericidal Action of LL-37: a Cathelicidin Found in Human Leukocytes and Epithelium", Oral Microbiol Immunol, 2000, vol. 15, pp. 226-231.

Van Houte, J., "Role of Micro-Organisms in Caries Etiology", J Dent Res, Mar. 1994, vol. 73, No. 3, pp. 672-681.

Wade, D. et al., "Antibacterial Peptides Designed as Analogs or Hydbrids of Cecropins and Melittin", Int. J. Peptide Protein Res., 1992, vol. 40, pp. 429-436.

Wüthrich, Kurt, "NMR of Proteins and Nucleic Acids", 1986, John Wiley & Sons, Inc., New York, pp. 44-92 and 117-199.

Yeaman, Michael R. et al., "Mechanisms of Antimicrobial Peptide Action and Resistance", The Pharmacological Reviews, 2003, vol. 55, No. 1, pp. 27-55.

Zasloff, Michael, "Antibiotic Peptides as Mediators of Innate Immunity", Current Opinion in Immunology, 1992, vol. 4, pp. 3-7.

Zasloff, Micahel, "Antimicrobial Peptides of Multicellular Organisms", Nature, Jan. 2002, vol. 415, pp. 389-395.

Zhao, Chengquan et al., "Identification of a New Member of the Protegrin Family by cDNA Cloning", FEBS Letters, 1994, vol. 346, pp. 285-288.

Faraj, Jabar A., et al., "Development of a Peptide-Containing Chewing Gum as a Sustained Release Antiplaque Antimicrobial Delivery System," AAPS PharmSciTech, 2007, vol. 8 (1).

Na, Dong Hee, et al., "Stability of Antimicrobial Decapeptide (KSL) and Its Analogues for Delivery in the Oral Cavity," Pharmaceutical Research, 2007.

Campanac, C., et al., "Interactions Between Biocide Cationic Agents and Bacterial Biofilms," Antimicrobial Agents and Chemotherapy, May 2002, pp. 1469-1474, vol. 46, No. 5.

Na, Dong Hee, et al., "Chewing Gum of Antimicrobial Decapeptide (KSL) as a Sustained Antiplaque Agent: Preformulation Study," Journal of Controlled Release, 2005, pp. 122-130, vol. 107.

\* cited by examiner

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial
<220> FEATURE:
<223> OTHER INFORMATION: Synthesis of Antimicrobial Peptide KSL

<400> SEQUENCE: 1

Lys Lys Val Val Phe Lys Val Lys Phe Lys
1               5                   10

<210> SEQ ID NO 2
<211> LENGTH: 10
<212> TYPE: PRT
<213> ORGANISM: Artificial
<220> FEATURE:
```

```
<223> OTHER INFORMATION: Synthesis of Antimicrobial Peptide KSL-W

<400> SEQUENCE: 2

Lys Lys Val Val Phe Trp Val Lys Phe Lys
1               5                   10

<210> SEQ ID NO 3
<211> LENGTH: 10
<212> TYPE: PRT
<213> ORGANISM: Artificial
<220> FEATURE:
<223> OTHER INFORMATION: Synthesis of Antimicrobial Peptide KSL-M
<220> FEATURE:
<221> NAME/KEY: MOD_RES
<222> LOCATION: (6)..(6)
<223> OTHER INFORMATION: METHYLATION

<400> SEQUENCE: 3

Lys Lys Val Val Phe Lys Val Lys Phe Lys
1               5                   10

<210> SEQ ID NO 4
<211> LENGTH: 25
<212> TYPE: PRT
<213> ORGANISM: Artificial
<220> FEATURE:
<223> OTHER INFORMATION: Synthesis of Antimicrobial Peptide H1-2

<400> SEQUENCE: 4

Asp Asp Asp Glu Glu Lys Phe Leu Arg Arg Ile Gly Arg Tyr Gly Lys
1               5                   10                  15

Lys Val Val Phe Trp Val Lys Phe Lys
            20                  25
```

ANTIMICROBIAL DECAPEPTIDE ORAL HYGIENE TREATMENT

The present application is a continuation-in-part of U.S. application Ser. No. 10/795,514, filed Mar. 9, 2004, now U.S. Pat. No. 7,494,980, which claimed the benefit of U.S. Provisional Application Ser. No. 60/455,206 filed Mar. 10, 2003, the content of all of which are hereby incorporated by reference in their entirety. This application also claims the benefit of U.S. Provisional Application Ser. No. 60/727,428 filed Oct. 18, 2005 and U.S. Provisional Application Ser. No. 60/735,915 filed Nov. 14, 2005, the contents of all of which are hereby incorporated by reference in their entirety.

A sequence listing is provided separately, both as a CRF on a compact disc, and as a separate paper copy. The Sequence Listing of the CRF is identical to the paper copy Sequence Listing.

I. FIELD OF THE INVENTION

The present invention relates to treatment of established biofilms by use of an antimicrobial decapeptide in conjunction with a surfactant or mechanical disruption. The present invention also relates to use of chewing gum containing an antimicrobial decapeptide as a sustained antiplaque agent. More particularly, the present invention relates to the use of KSL with surfactants or mechanical disruption in treating established oral biofilms and also chewing gum containing KSL for use as an oral hygiene treatment.

II. BACKGROUND OF THE INVENTION

Human oral biofilms are complex three-dimensional structures consisting of diverse and multispecies microbial communities formed on colonizable surfaces (Foster et al., 2004; Kolenbrander and London, 1993; Kolenbrander and Palmer Jr, 2004; Marsh and Bradshaw, 1995). Aside from the substrata's physical and chemical surface properties, which have a significant impact on bacterial accumulation (Quirynen et al., 2000), the formation of oral biofilms involves a series of events. This includes the initial formation of a conditioning saliva-derived film (the acquired salivary pellicle) on colonizable surfaces, the attachment of primary colonizers to host-derived receptor molecules present in the acquired pellicle, the subsequent interactions of secondary colonizers to the attached early colonizers, followed by the proliferation of the adhered bacteria (colonization), and the development of mature microbial communities (Kolenbrander and London, 1993; Marsh and Bradshaw, 1995; Quirynen et al., 2000). Uncontrolled growth of certain resident microbes in these communities may contribute to the development of oral diseases (Loesche, 1999).

The development of dental caries and periodontal diseases is closely associated with dental plaque, which is formed as a result of the adsorption of bacteria or their aggregates to the salivary pellicle formed on tooth surfaces. For the prevention and treatment of plaque-related oral diseases, there is a growing interest in the use of antimicrobial agents which act through bacteriocidal and/or bacteriostatic mechanisms. Among these agents are chlorhexidine, triclosan, metal ions, quaternary ammonium compounds and essential oils.

The salivary pellicle is formed through the selective adsorption of salivary proteins. The charged groups in the salivary proteins interact with charges of the opposite sign in the enamel and there is a predominance of negatively charged, acidic salivary proteins in the pellicle. Therefore, the affinity of the drug to teeth surfaces or acidic salivary proteins is an important factor for inhibiting the formation of plaque. Chlorhexidine is a bis-biguanide with strong cationic activity. It has been previously suggested that the binding of chlorhexidine to bacterial or acidic salivary components and subsequent retention on oral surfaces is directly related to the degree by which chlorhexidine can inhibit plaque growth. Although the chlorhexidine is regarded as the most efficacious antiplaque agent in current use, it has several disadvantages of bitter taste, impairment of taste perception, reversible staining of teeth and tongue and interaction with surfactants in the toothpastes.

In Applicant's co-pending application, U.S. Ser. No. 10/795,514, the contents of which are hereby incorporated by reference in its entirety, the present inventor discloses the discovery that the antimicrobial decapeptide KSL, and its analogs, may be used to prevent the formation of biofilms and may also be used to inhibit the growth of oral microorganisms.

While KSL showed usefulness in preventing the formation of oral biofilms, KSL did not have much affect on established biofilms. Moreover, while KSL was effective in inhibiting the growth of oral microorganisms, a reliable delivery method and treatment using KSL for oral hygiene had not been demonstratively shown. As will be appreciated, in situations where running water and toothbrushes are unavailable, methods of controlling plaque and oral biofilms are needed. For example, soldiers in the field may be asked to go days or weeks without brushing their teeth. Moreover, given the disadvantages of chlorhexidine, an antiplaque treatment having a more palpable taste with fewer side effects is needed to help ensure the treatment will actually be used.

The foregoing underscores some of the problems associated with treatment of established biofilms and using antimicrobial agents as an antiplaque agent. Furthermore, the foregoing highlights the long-felt, yet unresolved need in the art for a reliable formulation and method for treating established biofilms. The foregoing also highlights the long-felt, yet unresolved need in the art for a palpable formulation and method of treating plaque when brushing is impractical.

III. SUMMARY OF THE INVENTION

The present invention overcomes the practical problems described above and offers new advantages as well.

Recently, antimicrobial peptides isolated from a variety of natural sources have received attention because of their selectivity for prokaryotes and promise of minimizing microbial resistance. Analogues of these natural peptides have been synthesized with the goal of improving their antimicrobial activity. A novel antimicrobial decapeptide (KSL) was developed by using synthetic combinatorial library technology. This peptide and some of its analogs has been shown by the present inventor to possess a broad range of antibacterial activity as well as inhibit the growth of oral bacterial strains associated with caries development and plaque formation. The primary structure is as follows:

(SEQ ID NO:1)
[Lys-Lys-Val-Val-Phe-Lys-Val-Lys-Phe-Lys-NH$_2$]

The use of a chewing gum as a vehicle for antiplaque agents is appealing from a practical and compliance standpoint. The advantage of a gum is that it is usually kept in the mouth longer than rinses and toothpastes. The active agent included in a chewing gum, if successfully released into the saliva, would thus have ample time to bind to a variety of reception sites. As KSL is also a cationic molecule containing five lysine residues, it may have a potential for electrostatic interaction with teeth surface and acidic glycoproteins in saliva.

KSL has been previously shown to effectively blocked biofilm development, while remaining relatively ineffective on mature biofilms. The present inventor has discovered the unexpected result that KSL has a significant effect on the viability of mature biofilms when KSL is used in the presence of a surface-active agent, or after the biofilms are mechanically disrupted. Accordingly, the present invention shows that KSL may be a useful adjunct for conventional oral hygiene to prevent plaque-mediated dental diseases.

The present inventor has also discovered that the use of KSL in a chewing gum formulation does not suffer from the drawbacks of prior art antiplaque gums including bad taste, teeth staining, or inability to ensure sustained release.

Given the following enabling description and examples, the novel methods, means and compounds of the present invention should become evident to a person of ordinary skill in the art.

IV. BRIEF DESCRIPTION OF THE DRAWINGS

The present invention is described in conjunction with the following Figures wherein: The patent or application file contains at leas one drawing executed in color. Copies of this patent or patent application publication with color drawing(s) will be proved by the Office upon request and payment of the necessary fee.

FIG. 1 depicts a chewing apparatus and thermostatted test cell. The gum is placed between upper and lower surfaces. The chewing procedure consists of up and down strokes of the lower surface in combination with a shearing (twisting) movement of the upper surface.

Figure 8:
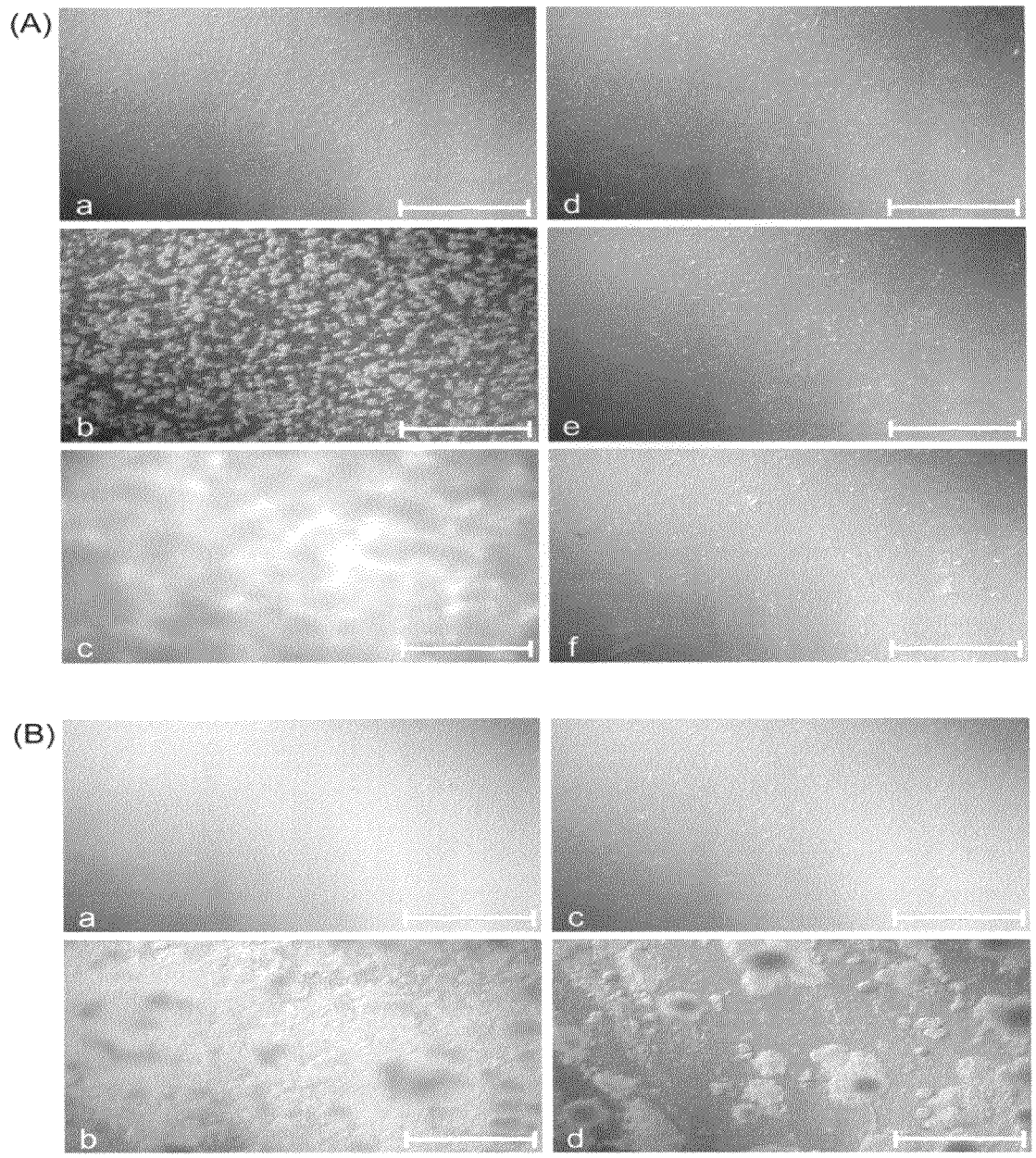

FIG. 8A is a schematic diagram of the dual flow cell model. (A) The flow system. Arrow heads indicate the direction of the flow. The system is connected by 14 gauge Masterflex tubing (Cole-Palmer, Vernon Hills, Ill.). For pulsed treatment of biofilms with KSL, a syringe pump (KD Scientific, Holliston, Mass.) with two injectable syringes containing respective treatment and control solutions is directly connected to each of the flow chambers through a three-way valve.

FIG. 8B depicts a dual flow cell. The flow cell consists of two parallel flow chambers each of which contain three recesses for holding Ge disks. The inner diameter and depth of each recess is 10.25 mm and 2.0 mm, respectively. Holes with a diameter of 2.0 mm for flow inlets and outlets are drilled in each end of the flow chamber. The flow chambers are contained on one side by the polycarbonate bottom plate and on the other side by an aluminum cover plate containing two parallel 60 mm×24 mm no. 2 cover glasses.

FIG. 8C is a cross section of the flow chamber showing the dimensions of the flow channel (0.4 mm deep, 13 mm wide, and 25 mm long).

Figure 9:
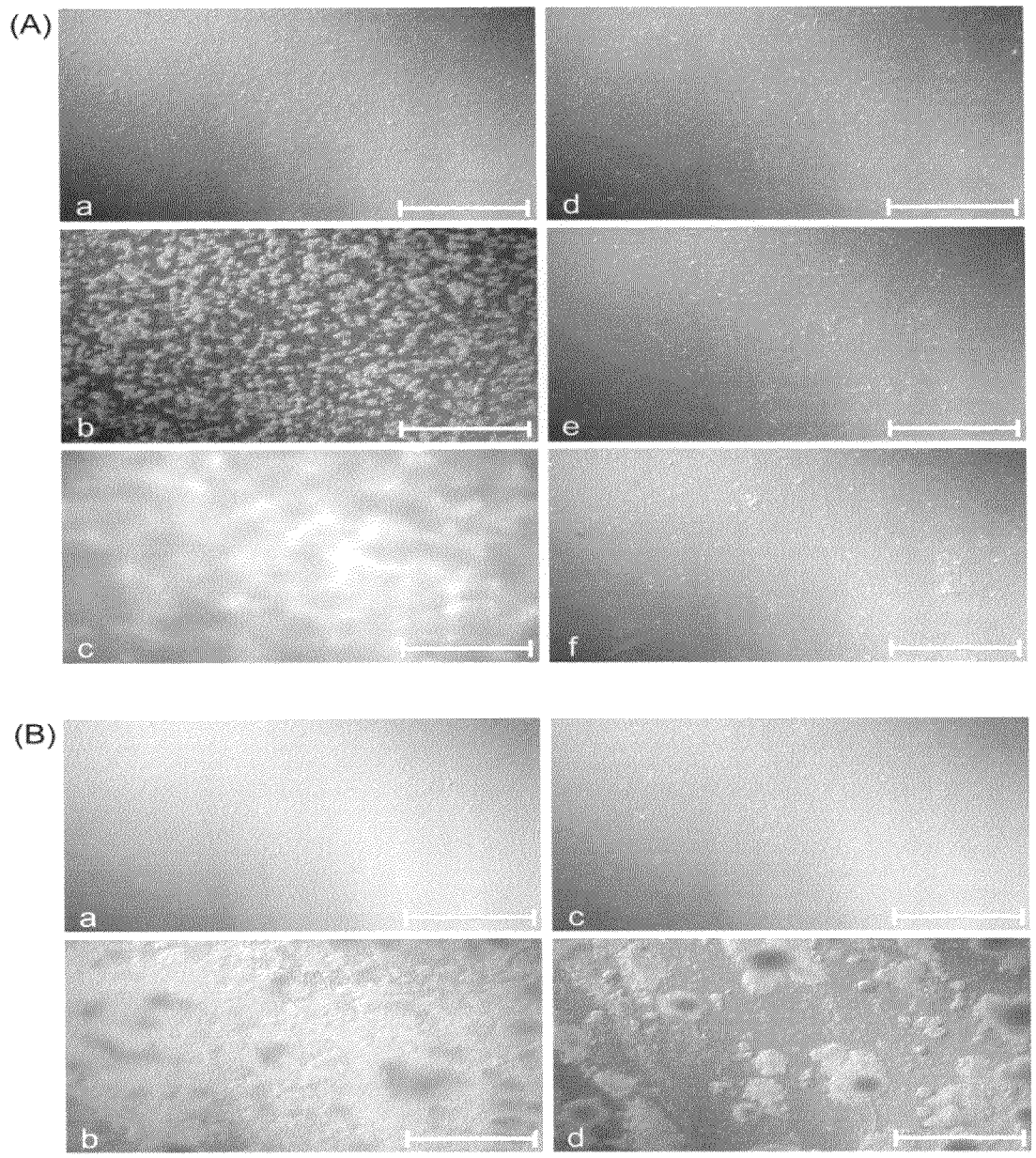

FIGS. 9A and B show the effect of KSL on oral biofilm development in a dual flow cell as revealed by DIC microscopy. (A) The continuous perfusion of a biofilm flow cell with KSL-containing (50 µg/ml µg/ml) medium prevents biofilm formation. Images of untreated biofilm cells (a-c, negative control) showing the development of biofilms from salivary bacteria adhered to saliva-conditioned Ge surfaces in the flow chamber perfused with KSL-free medium. Images of KSL (50 µg/ml µg/ml) treated biofilm cells (d-f). Side by side images of treated versus untreated were obtained at intervals of 2 h (a, d), 5 h (b, e), and 8 h (c, f) following inoculation of the parallel chambers of the dual flow cell. (B) Perfusion of the chamber with a lower concentration of KSL-containing medium (10 µg/ml µg/ml) was less effective in preventing biofilm formation. Untreated (a-b) and treated (c-d). Images were obtained at intervals of 2 h (a, c) and 8 h (b, d) following inoculation. Results represent one of the three experiments. Magnification, 200×. Bars represent 50 µm.

Figure 10:
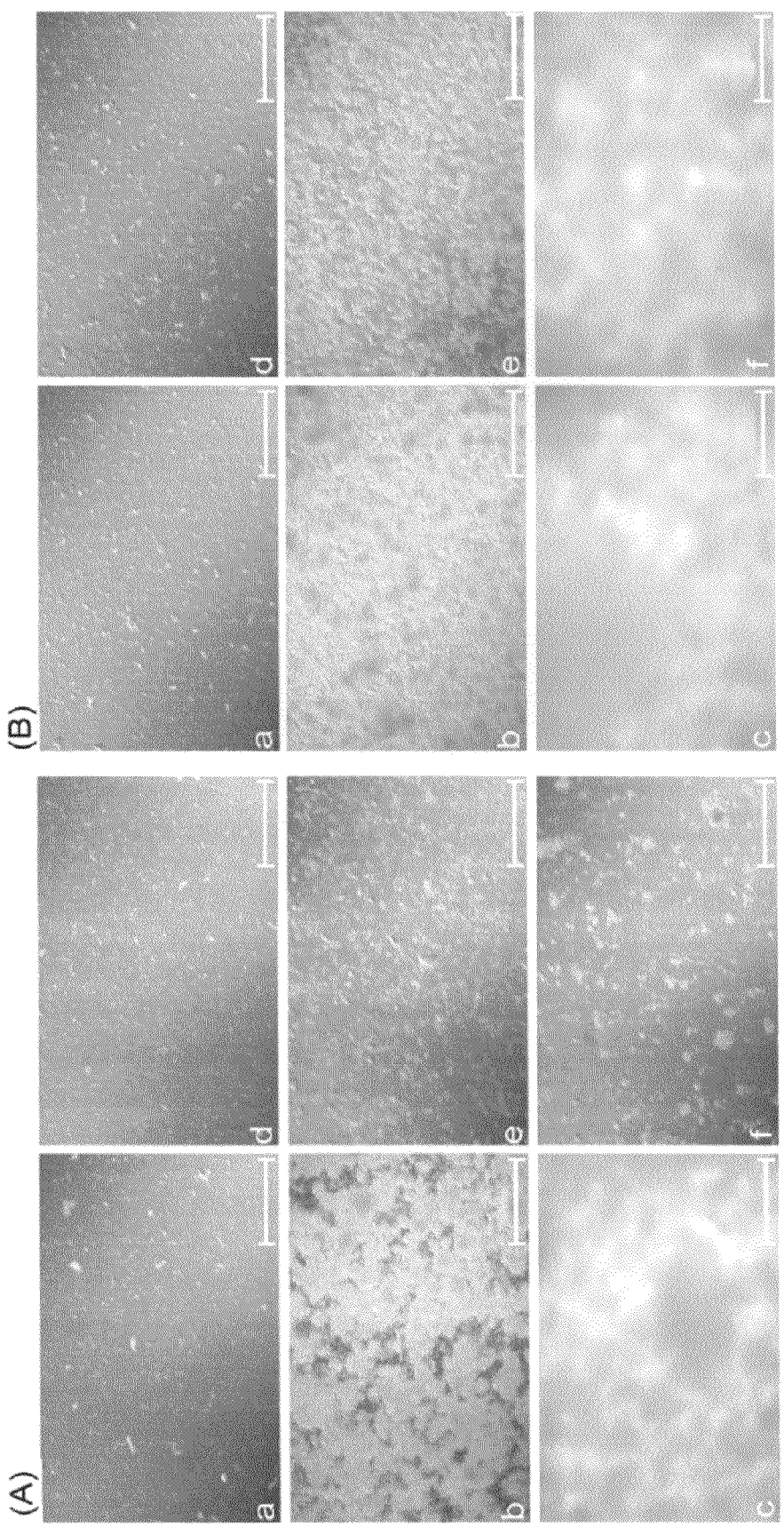

FIG. 10 shows DIC images of oral biofilm cells on Ge surfaces pulse-treated with KSL-free (a-c) and KSL-containing (50 µg/ml) medium (d-f). Pulsed treatment (30 min at 0.2 ml/min at 2 h intervals) initiated 4 h (A) or 6 h (B) after inoculation. Growth of biofilms was greatly inhibited in the flow chamber pulse-treated with KSL 4 h, but not 6 h, after inoculation. Images of treated versus untreated biofilm cells were obtained at intervals of 2 h (a, d), 6 h (b, e), and 10 h (c, f) after inoculation of salivary bacteria into the parallel chambers of the dual flow cell. The data represent the results of one of the three separate experiments. Magnification, 200×. Bars represent 50 µm.

Figure 11:
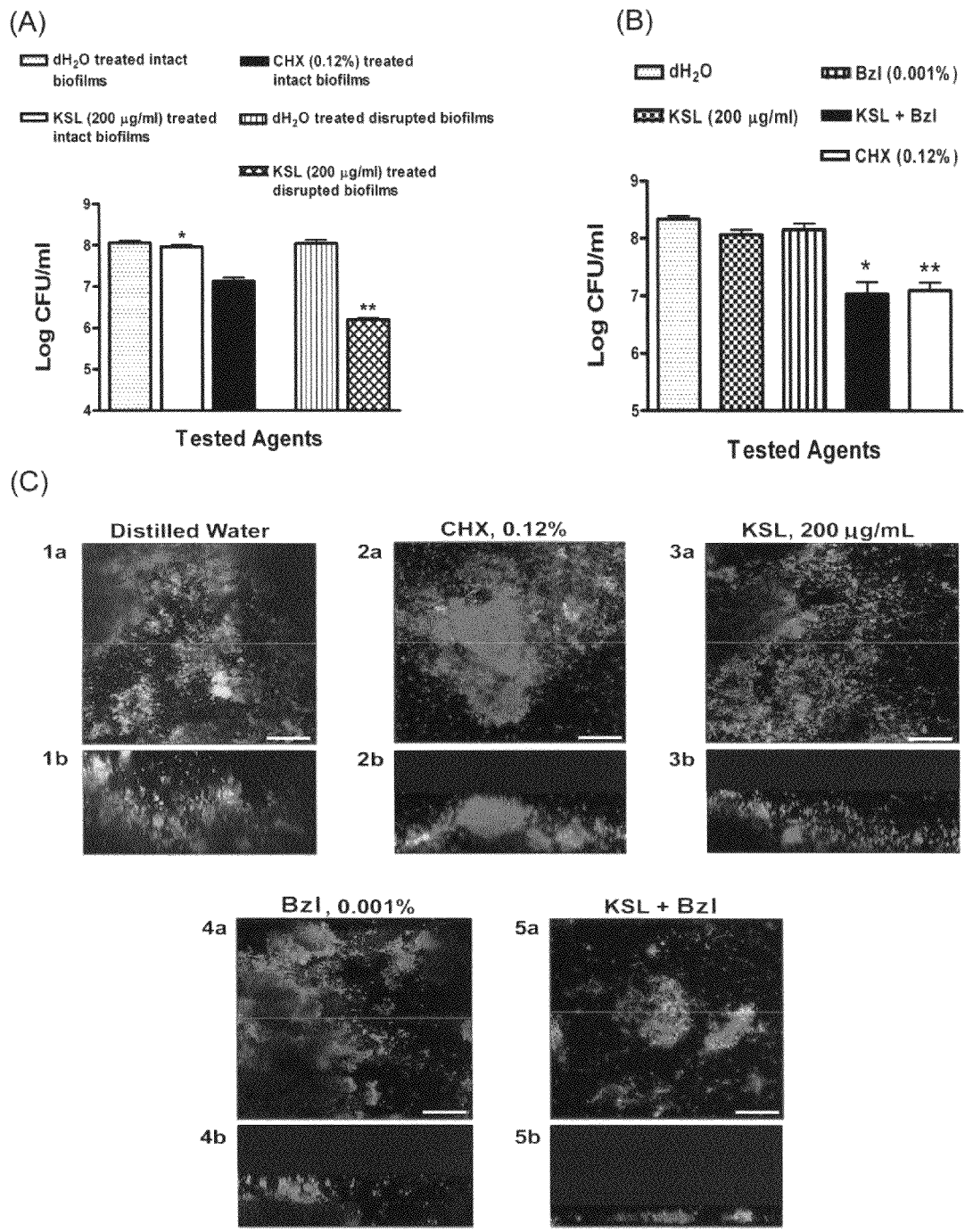

FIG. 11 shows the effect of KSL on intact versus disrupted biofilms and the effect of KSL with surfactant on biofilms. (A) Effect of KSL on intact versus disrupted 45 h biofilms formed on saliva-coated HA disks by salivary bacteria using the in vitro plaque assay. A Mann-Whitney test was used for comparison of log reductions in CFU between the experimental groups (KSL-treated intact or disrupted biofilms) with the control groups ($dH_2O$-treated intact or disrupted biofilms). The single asterisk represents a statistically significant difference between KSL and $dH_2O$-treated intact biofilms ($p<0.05$). Likewise, double asterisks represent a statistically significant difference between KSL and $dH_2O$-treated disrupted biofilms ($p<0.01$). While KSL caused slight reductions in CFU of treated, intact biofilms, chlorhexidine (CHX) caused more reduction in viability of intact biofilms. (B) Effect of benzalkonium chloride in promoting the bactericidal activity of KSL against 66 h-old intact oral biofilms formed on saliva-coated HA disks using the in vitro plaque system. A Kruskal-Wallis test was used to compare log reductions in CFU among various treatment groups including the control group ($dH_2O$-treated). The single asterisk represents a statistically significant difference between the combined treatment of KSL and benzalkonium chloride (Bzl) and $dH_2O$ ($p<0.001$), KSL ($p<0.01$), or Bzl ($p<0.01$)-treated intact biofilms. Double asterisks represent a statistically significant difference between CHX and $dH_2O$ ($p<0.001$) or Bzl ($P<0.05$)-treated intact biofilms. While KSL or Bzl alone, as compared to the dH₂O-treated group, caused no significant reductions in viability of intact biofilms, the combined use of KSL and Bzl had a significant effect on the viability (over one log reduction of viable counts) of these 66 h-old oral biofilms. No significant difference in viability counts was observed between CHX-treated versus the combined use of KSL and Bzl. For (A) and (B), the data represent the determinations of one of three separate experiments, each performed in quadruplicate. Bars represent standard deviations. (C) Confocal images of control and treated biofilms grown on saliva-coated HA surfaces. Live/Dead BacLight™ Viability kit (Molecular Probes, Eugene, Oreg.) was used to assess the viability of biofilm cells exposed to different treatments. BacLight assay solution was prepared as described by the manufacturer and the specimens were stained in dark at room temperature for 15 min. After washing 3× with water, samples were observed with an Axioplan light microscope fitted with an Ar—Kr laser (Zeiss LSM 510 Meta) and water immersion (long working distance) objectives. An excitation wavelength of 488 nm was used and the fluorescence light emitted was collected by two separate emission filters, 500-530 nm (SYTO 9, live), and 650-710 nm (propidium iodide, dead). As compared to the control (1a and b), which showed mostly green staining biofilm cells (indicating live), CHX (2a and b) or combined use of KSL and Bzl (5a and b) significantly reduced the viability of biofilm cells indicated by the presence of mostly red staining biofilm cells (indicating dead). KSL (3a and b) or Bzl (4a and b) alone at indicated concentrations had less impact on the viability of biofilm cells. Panels 1a-5a represent horizontal (xy) sections through biofilms, whereas panels 1b-5b are sagittal (xz) images of biofilms (indicated by the line on the horizontal xy sections) treated with different agents. Bars represent 50 μm.

Figure 12:
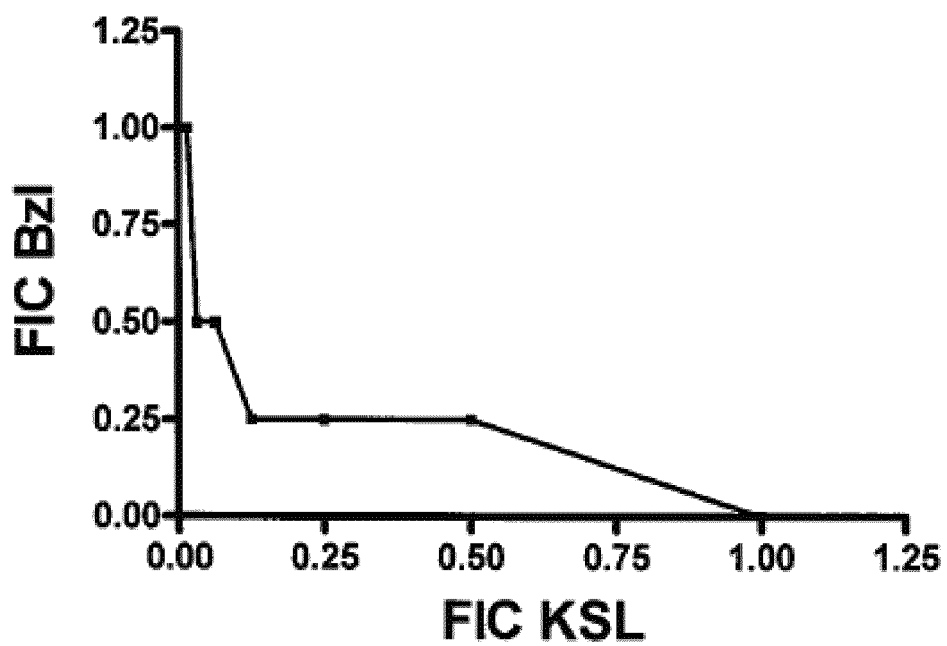

FIG. 12 shows synergistic interactions of KSL and benzalkonium chloride (Bzl) in killing salivary bacteria.

Figure 13:
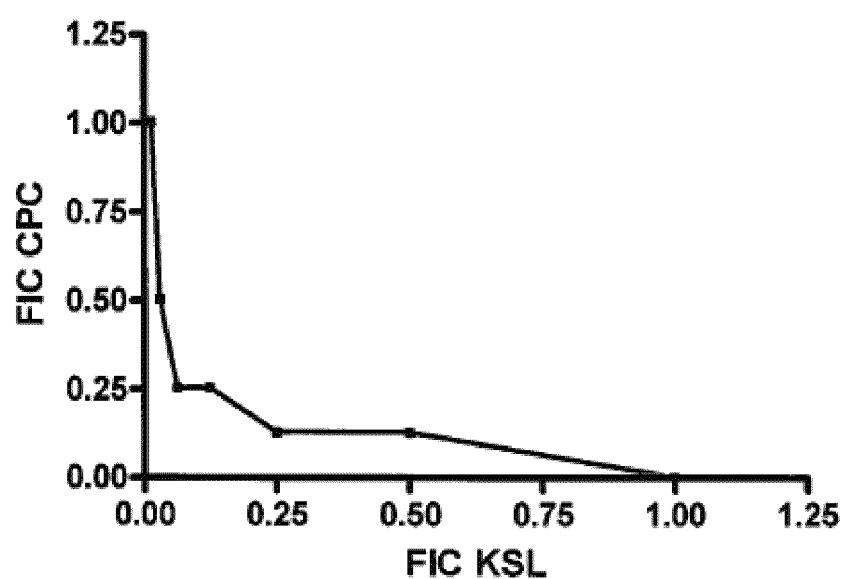

FIG. 13 shows synergistic interactions of KSL and cetylpyridinium chloride (CPC) in killing salivary bacteria.

Figure 14:
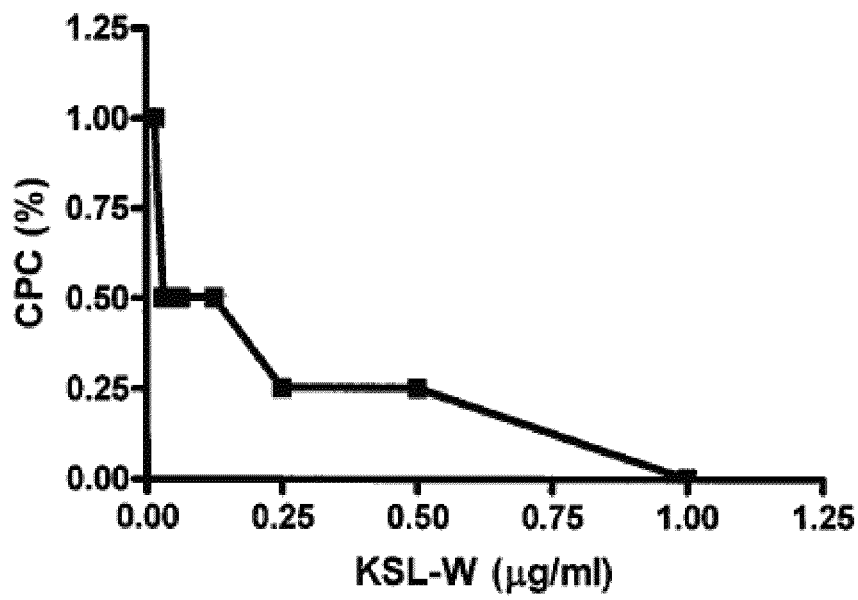

FIG. 14 shows synergistic interactions of KSL-W and cetylpyridinium chloride (CPC) in killing salivary bacteria.

Figure 15:
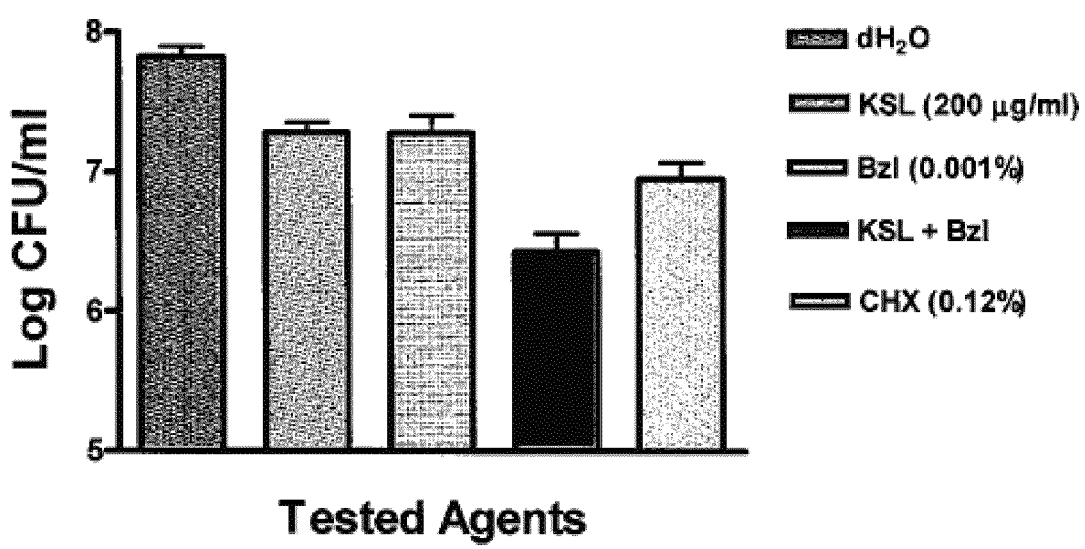

FIG. 15 shows effect of benzalkonium chloride in promoting the bactericidal activity of KSL against 45 h-old intact oral biofilms formed on saliva-coated HA disks using the in vitro plaque system. Biofilms were treated once with test agents prior to the determination of the viability of the biofilm cells recovered from the treated disks. CFU, colony-forming units.

Figure 16:
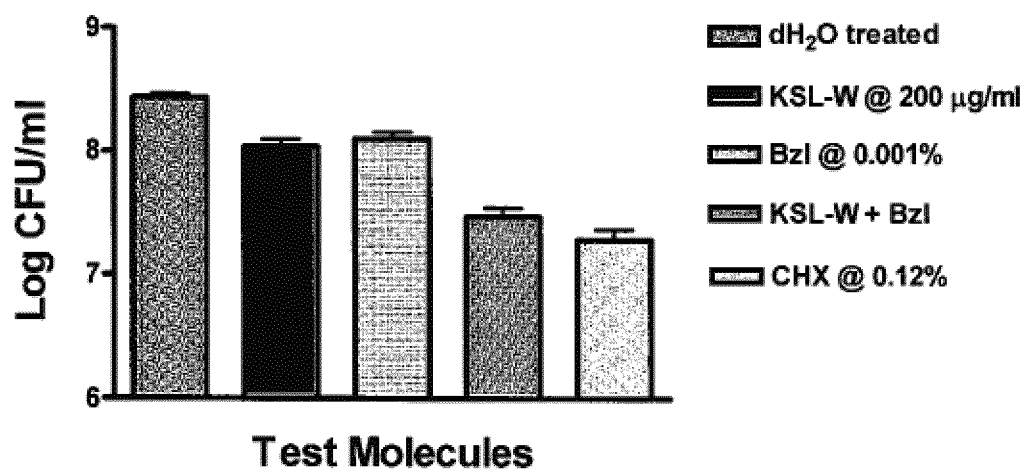

FIG. 16 shows effect of benzalkonium chloride in promoting the bactericidal activity of KSL-W against 45 h-old intact oral biofilms formed on saliva-coated HA disks using the in vitro plaque system. Biofilms were treated once with test agents prior to the determination of the viability of the biofilm cells recovered from the treated disks. CFU, colony-forming units.

Figure 17:
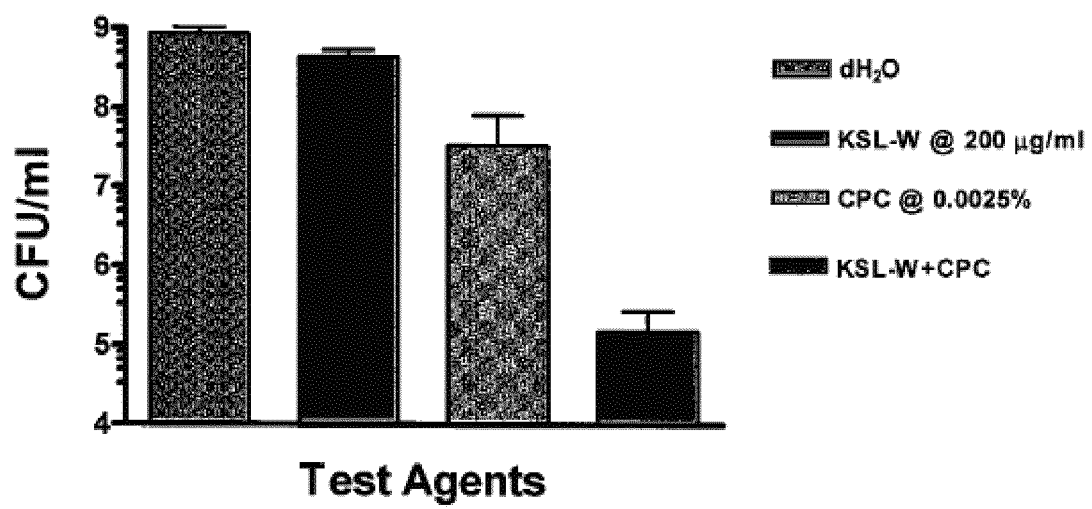

FIG. 17 shows effect of cetyl pyridinium chloride in promoting the bactericidal activity of KSL-W against 66 h-old intact oral biofilms formed on saliva-coated HA disks using the in vitro plaque system. The 66 h-old biofilms were treated three times (within 24 h) with test agents prior to the determination of the viability of the biofilm cells recovered from treated disks. CFU, colony-forming units.

Figure 18:
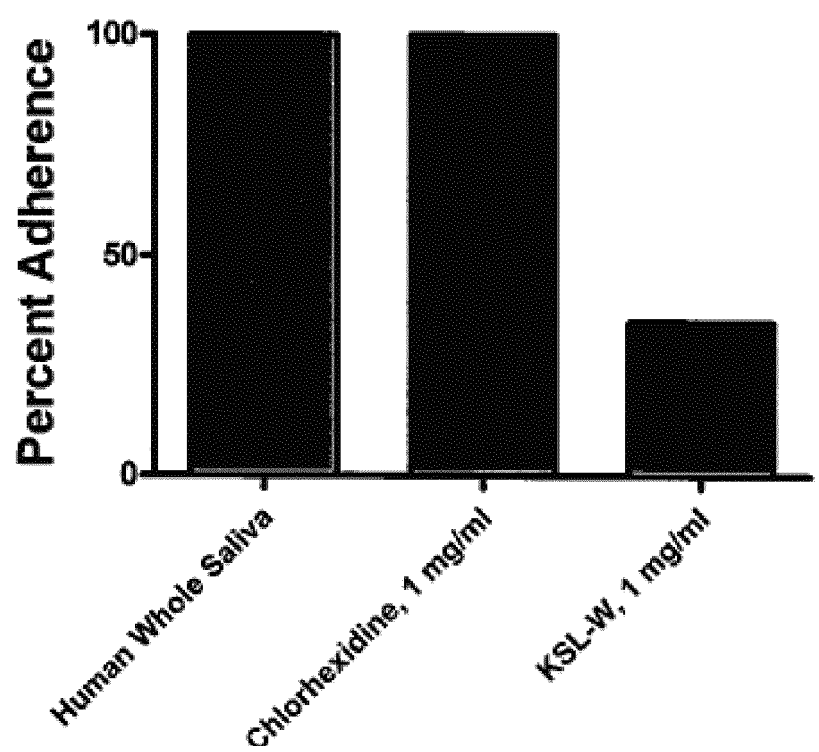

FIG. 18 shows inhibition of tritiated *A. naeslundii* adhering to HA surfaces pretreated with KSL-W.

V. DETAILED DESCRIPTION

The present invention is based, in part, on the discovery that KSL, and its analogs, have a synergistic effect on treating mature biofilms when coupled with a surface-active agent. These unexpectedly and surprising results are set forth in the examples below. According to this aspect of the invention, KSL in combination with a surface active agent may be part of method of preventing and treating growth of oral microorganisms, mature biofilms, and in particular dental caries and plaque. This aspect of the invention may prove useful in oral hygiene formulations for oral hygiene and treatment in environments where brushing is not a viable option.

The present invention is also based, in part, on the discovery that KSL, and its analogs, may be used to treat mature biofilms when used in conjunction with mechanical disruption of the biofilms. These unexpectedly and surprising results are also set forth in the examples below. According to this aspect of the invention, KSL in combination with mechanical disruption, such as brushing, may be part of method of preventing and treating growth of oral microorganisms, mature biofilms, and in particular dental caries and plaque. This aspect of the invention may prove useful as part of a universal oral hygiene treatment program.

The present invention is also based, in part, on the discovery that KSL, and its analogs, may be used in chewing gum formulations to provide a sustained antiplaque agent. The unexpected and superior results of KSL chewing gum formulations are set forth in the examples below. According to this aspect of the invention, KSL and derivatives thereof may be part of a chewing gum formulation to hinder and prevent plaque formation and promote better oral hygiene. This feature of the invention is particularly advantageous to promote better oral hygiene to individuals that cannot or do not brush their teeth, such as soldiers in the field.

The following examples will further clarify various advantageous features and unexpected results of the present invention.

A. Chewing Gum of Antimicrobial Decapeptide (KSL)

1. Materials and Methods 1.1. Materials

KSL (MW=1250 Da) was synthesized by standard solid-phase procedures using 9-fluorenylmethoxycarbonyl (Fmoc) chemistry on an automatic peptide synthesizer (Model 90, Advanced ChemTech, Louisville, Ky.) and its purity determined as previously described [7]. Gum base (SMILY 2A) was obtained from Gum Base Co. (Milano, Italy). D-sorbitol and d-mannitol were obtained from Sigma (St. Louis, Mo.). Acetonitrile (HPLC grade) and dimethyl sulfoxide (DMSO) was purchased from Fisher Scientific (Fair Lawn, N.J.). Trifluoroacetic acid (TFA) was obtained from Pierce (Rockford, Ill.). All other chemicals were of analytical grade and used as obtained commercially.

1.2. High-Performance Liquid Chromatography Analysis of KSL

KSL was analyzed by RP-HPLC using a Prosphere C-18 analytical column (4.6×250 mm, Alltech, Deerfield, Ill.) with a Prosphere C-18 guard column (4.6×7.5 mm, Alltech, Deerfield, Ill.). A gradient elution was performed with mobile phase A (0.1% TFA in water) and mobile phase B (0.1% TFA in acetonitrile). KSL was eluted with a linear gradient from 80:20 to 70:30 (mobile phase A:B) for 8 min at a flow rate of 1.0 ml/min. Total run time was 16 min and the injection volume was 40 μl. Chromatograms were recorded by UV detection at 215 nm.

1.3. Stability Study

Test solutions of KSL were prepared using a stock peptide solution of 10 mg/ml in deionized water. The degradation of KSL peptide was investigated in sodium acetate (pH 4), sodium phosphate (pH 7.4) and sodium borate (pH 9) buffers at 0.1 M buffer concentration. Each buffer solution containing 200 µg/ml of KSL was incubated in a temperature-controlled oven at 25, 37 and 55° C., respectively. Samples were taken at pre-determined times and analyzed under HPLC conditions described above. The stability of KSL was studied at 37° C. in artificial saliva over a three day period. Artificial saliva was used in the in vitro release studies in an attempt to simulate actual conditions of use. The ingredients of the artificial saliva were as follows: sodium chloride, 0.844 g; potassium chloride, 1.200 g; calcium chloride dihydrate, 0.193 g; magnesium chloride hexahydrate, 0.111 g; potassium phosphate dibasic, 0.342 g; water to make to 1000 ml. The pH was adjusted with hydrochloric acid solution to pH 5.7±0.1 [26].

1.4. Interaction with Hydroxyapatite Discs

Affinity of KSL to tooth-like materials was assessed by allowing the KSL to interact with HA discs (Size: 0.38" diameter×0.06-0.08" thick) in artificial saliva at 37° C. To simulate the tooth surface, the HA discs were pretreated in filtered human saliva for 2 hours (4 HA discs/4 mL of human saliva). Whole human saliva was collected from three healthy male donors in the morning prior to breakfast. After collection, the saliva was immediately centrifuged at 12,000 rpm for 20 min and the supernatant was filter through a 0.45 µm membrane filter. The HA discs, after conditioning with human saliva, were rinsed with artificial saliva and added to 4 ml of KSL solutions (0.5 mg/ml in artificial saliva) at 37° C. As a control, untreated HA discs were directly added to KSL solutions at 37° C. The sample vials were mounted on a rotary wheel with vertical rotation at a speed of 18 cycles/min. Samples were removed at predetermined times, centrifuged and the supernatants were analyzed by RP-HPLC.

1.5. Chewing Gum Preparation

The chewing gum formulations were prepared following a procedure described previously [8]. The gum base was heated at a temperature between 50 and 60° C. for melting. When the gum base was of the proper fluid consistency, the KSL was added as a fine powder along with the other components. The temperature was kept constant while mixing the components with the gum base in a mortar. After mixing, the homogenous chewing gum mixture was extruded, cut into squares of approximate shape and size and hardened at room temperature overnight. The composition of the gum was as follows: 550 mg of gum base, 420 mg of sorbitol, 10 mg of mannitol, 10 mg of saccharin, and 10, 20 or 30 mg of KSL (total weight: approximately 1 g).

1.6. In Vitro Release Study

Figure 1:
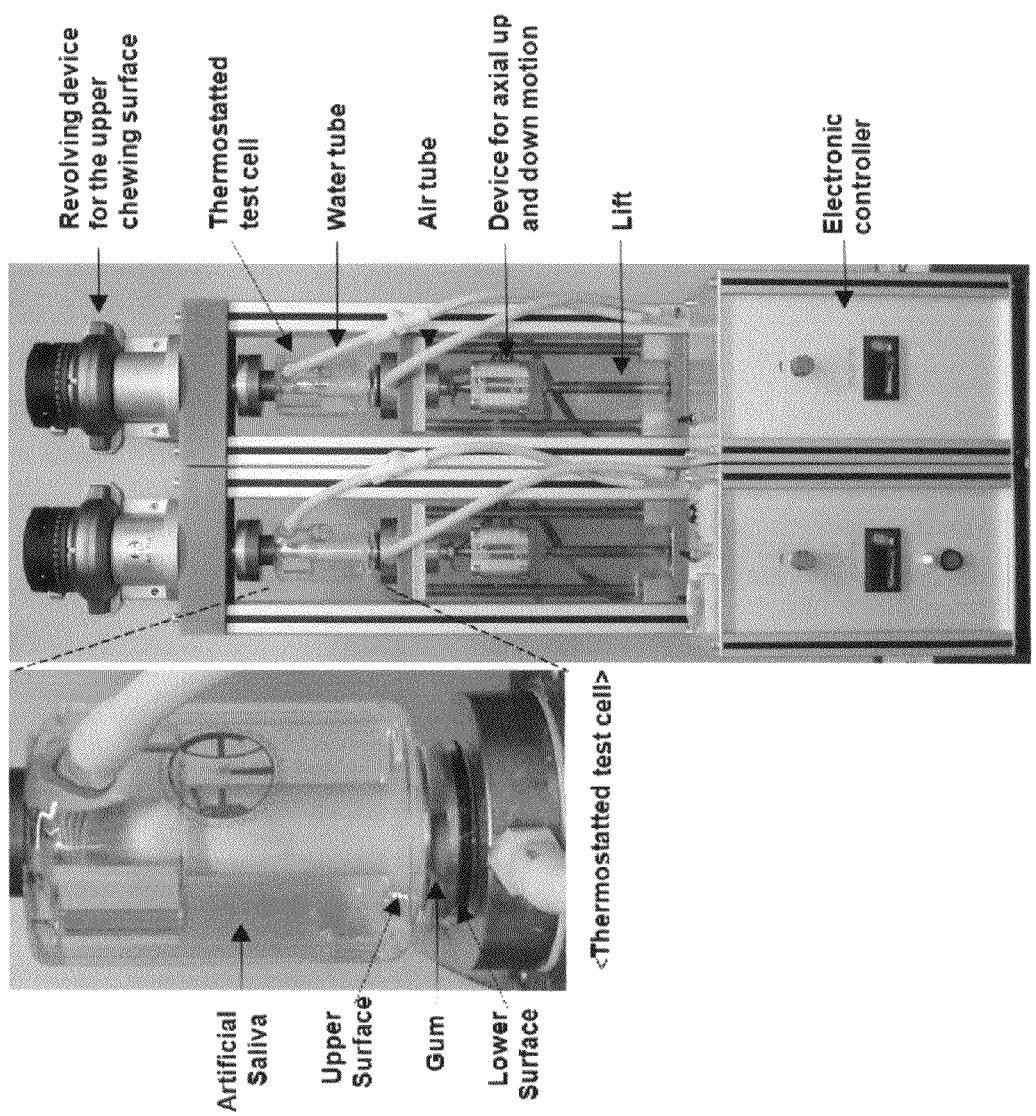

In vitro release study of KSL from chewing gums was carried out using an in vitro chewing release apparatus consisting of two modules (AB FIA, Lund, Sweden) (FIG. 1). Each module consists of a thermostatted glass cell in which two vertically oriented pistons holding an upper and a lower chewing plate are mounted. The cells were filled with 40 ml of artificial saliva and the chewing gum was loaded onto the lower chewing surface. The chewing procedure consisted of up and down strokes of the lower surface in combination with a twisting movement of the upper surface; this action provides mastication of the chewing gum and agitation of the test medium. The temperature of the test medium was controlled at 37° C. and the chew frequency was 50±2 strokes per min. At predetermined time intervals, 400 µl of supernatant were removed. The dissolution medium was replaced with fresh artificial saliva after each sampling. The released amount of KSL was determined by RP-HPLC.

1.7. In Vivo Release Study

A chew-out study was performed with three volunteers. Each volunteer masticated one piece of each kind of gum at 30-40 chews/min for given periods of time (5, 10 and 20 min). After chewing the gum for a predetermined period of time, the remaining amount of KSL in the gum was analyzed. To extract the KSL, the gum was heated to 50-60° C. for 5 min and then 5 ml of a mixture of acetonitrile and DMSO (1:1) were added. After fully mixing for 5 min, 10 ml of 0.1 M acetate buffer (pH 4) were added and the mixture was vigorously shaken for 30 min at room temperature. The sample was centrifuged and the supernatant was filtered into HPLC vials with a 0.45 µm membrane filter.

2. Results and Discussion 2.1. HPLC Analysis of KSL

Figure 2:
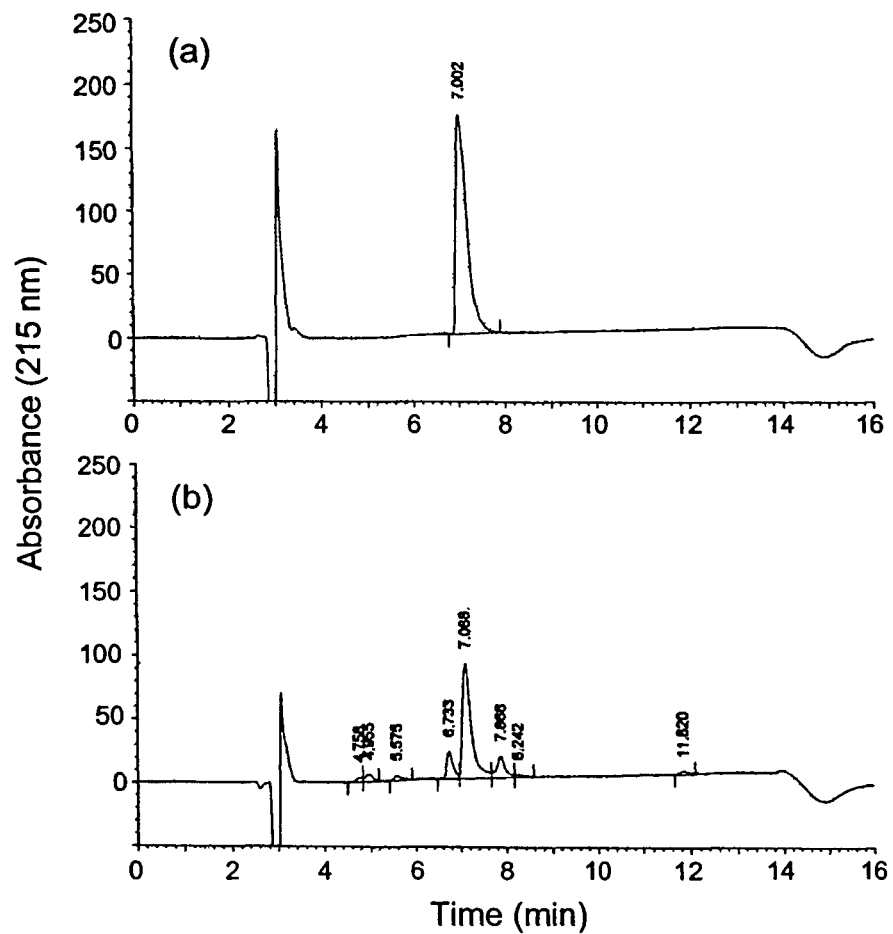
FIG. 2 depicts RP-HPLC chromatograms of KSL standard in water (a) and incubated in 0.1 M borate buffer (pH 9) at 55° C. for 3 days (b).

As an analytical method for KSL, the reversed-phase HPLC method using gradient elution has been developed. Under the HPLC conditions, the standard of KSL in deionized water was detected as a single peak at a retention time of 7.0 min (FIG. 2a). The correlation coefficient of the linearity for the detection of KSL was greater than 0.999 in a peptide concentration range of 20-400 µg/ml and the assay was reproducible at these concentrations with a coefficient variation <5% (n=3, intra- and inter-assay). The HPLC method was able to resolve intact KSL from the degradation compounds produced in sodium borate buffer (pH 9) at 55° C. for 3 days (FIG. 2b). No attempt was made to identify degradation products or determine a degradation pathway, which quite possibly involved peptide bond breaking and oxidation as described previously [27].

2.2. Chemical Stability in Aqueous Solutions

Figure 3:
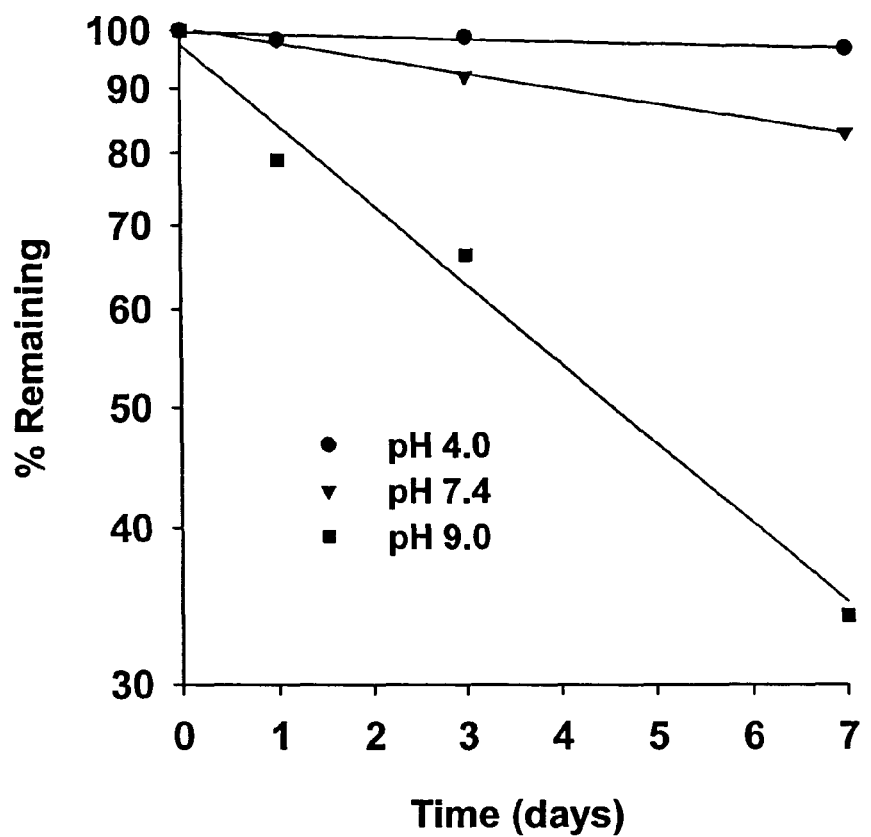
FIG. 3 depicts the degradation kinetics of KSL in different pH conditions at 55° C.
Figure 4:
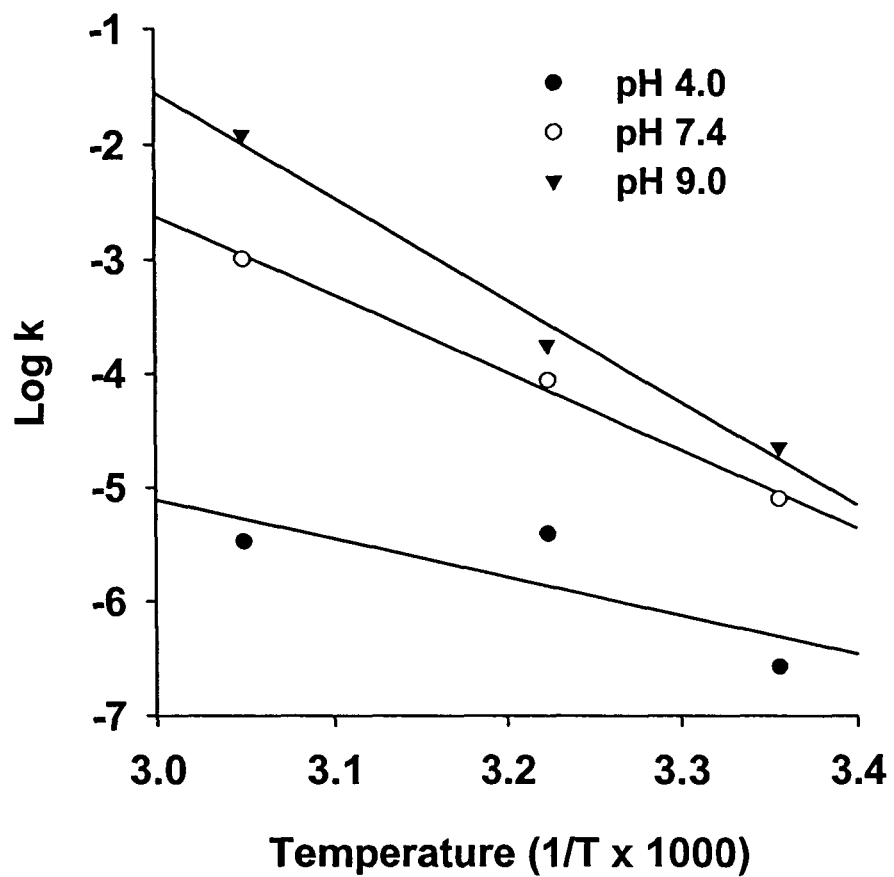
FIG. 4 depicts the Arrhenius plot for the degradation of KSL in different pH buffers.

FIG. 3 shows a semilogarithmic plot of the residual percentage amount of KSL versus time in various pH solutions at 55° C. The pH affected the degradation rate of KSL with the observed degradation reaction rates approximately following first-order kinetics. The degradation of KSL was also studied in buffer solutions from 25 to 55° C. Degradation rate constants were obtained from the slope of the semilog plots of the concentration versus time data by regression analysis. The observed reaction first-order rate constants of KSL are listed in Table 1. Although the optimum pH for KSL stability was not defined, the most favorable stability appeared to be in acetate buffer, pH 4. The half-life for KSL degradation at 55° C. was 165.0 days at pH 4, 13.8 days at pH 7.4, and 4.7 days at pH 9. The relationship between temperature and rate constant is shown by Arrhenius plots in FIG. 4. Activation energies ($E_a$) derived from the slope were 6.7 kcal/mol at pH 4, 13.6 kcal/mol at pH 7.4 and 17.9 kcal/mol at pH 9 (Table 1). KSL was also stable in artificial saliva (data not shown). After the incubation for 3 days at 37° C., there was no degradation peak detected by HPLC.

2.3. Interaction with HA Discs

Figure 5:
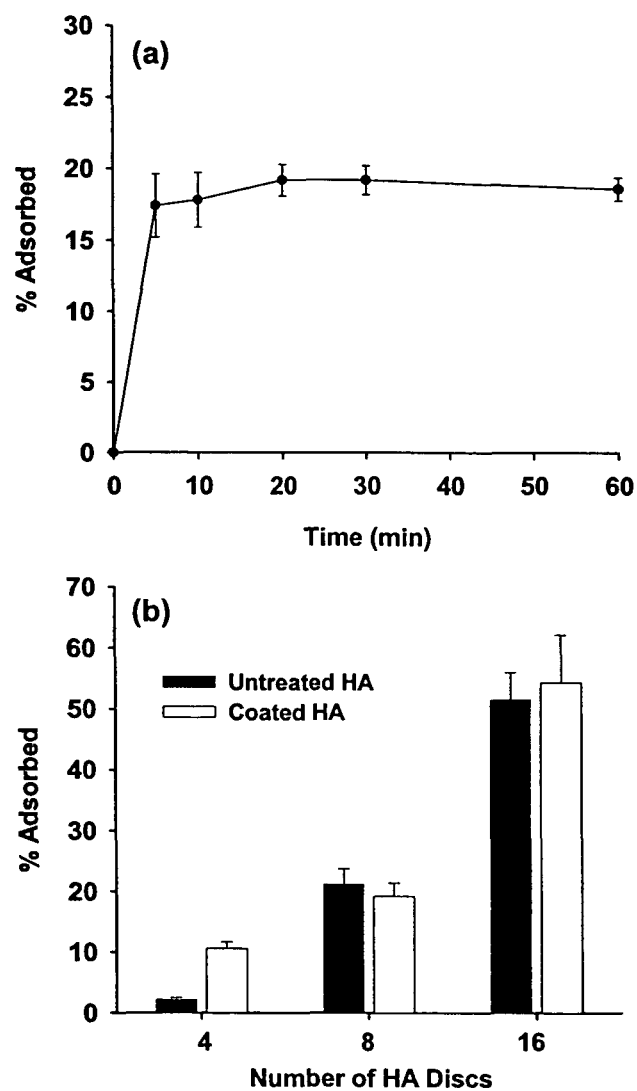
FIG. 5 depicts adsorption of KSL to HA discs in artificial saliva at 37° C. wherein (a) is the adsorption profile of KSL (0.5 mg/ml) to 8 untreated HA discs and (b) is the adsorption of KSL to untreated and pretreated HA discs for 20 min. The pretreated HA discs were soaked in human saliva for 2 h at 37° C., and then washed with artificial saliva, dried and added to KSL solutions.

The affinity of KSL to tooth-like materials and salivary proteins using HA discs is shown in FIG. 5. FIG. 5a shows that adsorption equilibrium occurred within 5 min and approximately 20% of the KSL adsorbed to 8 discs. The adsorption of KSL was dependent on the amount of HA discs and the protein coating on the discs (FIG. 5b). In comparing the untreated and protein-coated HA discs by soaking in human saliva, there was discernible difference in binding when 4 HA discs were used. This may be due to the limited number of binding sites and the greater adsorption to the coated HA discs. This suggests that the acidic salivary proteins might play a role because KSL is a cationic molecule containing five lysine residues and thus has a great potential for electrostatic interaction with acidic glycoproteins in saliva. It has been strongly suggested that the retention of chlorhexidine in the oral cavity is directly related to the inhibition of plaque formation [17-19]. Barnett et al. reported a correlation of chlorhexidine binding to HA with in vivo antiplaque efficacy [28]. As shown in this study, the affinity of KSL to the HA suggests its potential as an antiplaque agent together with antimicrobial activity on oral bacteria strains that are associated with plaque formation [7].

2.4. In Vitro Release from Chewing Gum

Devices and methods for in vitro dissolution and drug release testing have been described for solid dosage forms [23]. However, these methods are not easily adapted for studying the release of drug from chewing gums because continuous mastication is needed for the drug release. The apparatus developed by Kvist et al. showed usefulness for in vitro drug release testing of chewing gum formulations [24, 25].

Figure 6:
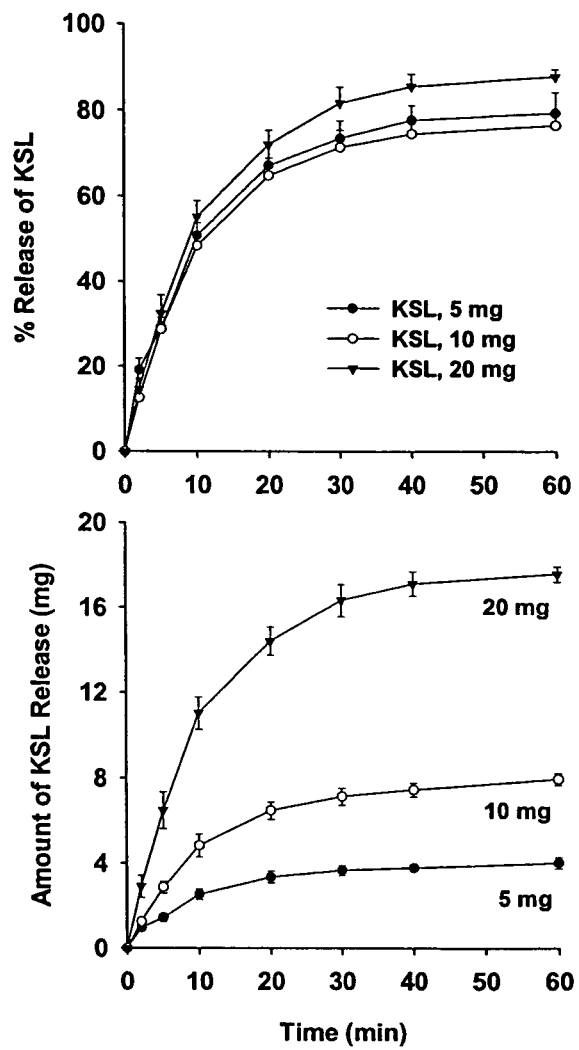
FIG. 6 shows in vitro release of KSL from gum formulations in artificial saliva at 37° C. The chewing gums containing different KSL loadings (5, 10, 20 mg) were studied using a chewing apparatus.

FIG. 6 shows the in vitro release profiles of KSL from chewing gum formulations containing different amounts of peptide (5, 10 and 20 mg per gum). The release of KSL from three gum formulations showed 48-55% at 10 min, 65-72% at 20 min, and 71-82% at 30 min. The gum formulation containing 20 mg of KSL showed a slightly higher % of release than the gums containing 5 and 10 mg of KSL. Totally, 78-88% of KSL was released for 60 minutes. The amount of released KSL was proportional to the loading level of the gum formulations.

The in vitro release test was effective for assessing the stability of KSL in the gum formulations manufactured at 50-60° C. HPLC analysis of KSL released from the gums showed only an intact KSL peak, which indicates that the peptide remains stable during the manufacturing process (data not shown).

2.5. In Vivo Release from Chewing Gum

In vivo chew-out study was performed to correlate the drug release pattern between the in vitro results and the in vivo performance. The gum was chewed by trained volunteers for 5, 10, 20 min, respectively, and then the residual KSL was extracted from the chewed gum. To validate the extraction method, the gums containing each 10, 20 and 30 mg of KSL were tested. The extraction yields of the three gums were within 84.3-88.6% relative to the loading amount. HPLC analysis of the extracted KSL showed a single peak at the same retention time as the standard KSL.

Figure 7:
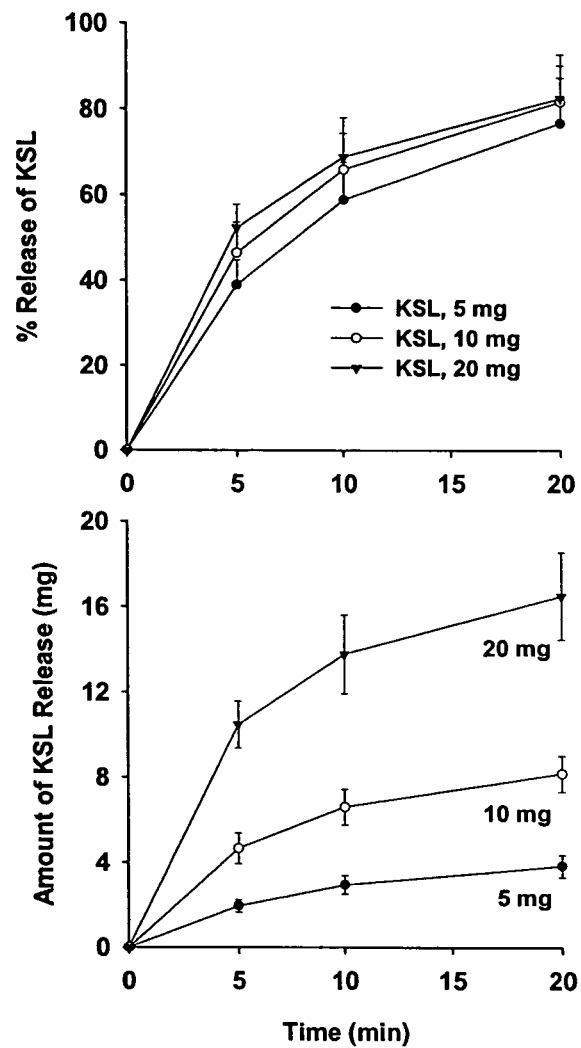
FIG. 7 shows in vivo release of KSL from gum formulations by a chew-out study. Volunteers chewed each gum containing 5, 10 or 20 mg of KSL for the predetermined times and the residual amount was extracted and analyzed by RP-HPLC.

FIG. 7 shows the in vivo release profiles of KSL from the same chewing gum formulations used for in vitro release study. The % release of KSL from three gum formulations was not significantly different at each time point and showed 39-52% release at 5 min, 59-69% at 10 min, and 77-83% at 20 min. Similar to the in vitro release, the amount of released KSL was proportional to the loading level. Although the released amount of KSL in the in vivo study was slightly higher than the in vitro release, the release patterns were essentially the same. The correlation coefficient of in vitro and in vivo release was >0.99. Previously, Kvist et al. also reported that the in vitro release profile obtained by using the same apparatus was very similar to the in vivo release profile [25]. Consequently, the chewing gum formulations containing KSL showed favorable in vitro/in vivo release profiles, which reached nearly 80% release in 20 min. Twenty minutes of chewing time has been reported to be the usual time for more than 80% of the American gum chewers [29].

KSL showed high affinity to HA discs pretreated with human saliva and was successfully formulated in a chewing gum. Promising release profiles were obtained in vitro using the chewing apparatus and in vivo by the chew-out method. This study suggests that the KSL will be released from the chewing gum in a controlled manner and effectively retained in the oral cavity to inhibit the formation of dental plaque.

B. Control of Oral Biofilms

1. Materials and Methods 1.1 Synthesis of the Antimicrobial Decapaptide, KSL

KSL (KKVVFKVKFK-NH2) [SEQ ID NO: 1] was synthesized by standard solid-phase procedures using 9-fluorenylmethoxycarbonyl (Fmoc) chemistry on an automatic peptide synthesizer (Model 90, Advanced ChemTech, Louisville, Ky.) and its purity determined as previously described (Concannon et al., 2003).

1.2 Buffers and Media

An artificial saliva buffer was prepared as previously described (Shellis, 1978). A saliva-based medium described by Williams (Williams, 1998) was used for the in vitro plaque assay system.

1.3 Collection of Saliva and Isolation of Salivary Bacteria

The procedures for collecting human saliva and isolating salivary bacteria were previously described (Concannon et al., 2003). The study was approved by the Institutional Review Board of the Walter Reed Army Institute of Research and informed consent was obtained from all volunteers.

1.4 Dual Flow Cell System

The dual flow cell system used in this study was modified from the chemostat flow cells of Herles et al. (Herles et al., 1994) and constructed according to our design and specifications by BioSurface Technologies (Bozeman, Mont.) (FIG. 1). The flow cell consisted of two compartments, each containing a polycarbonate flow chamber with three recesses to hold the Ge disks (10 mm in diameter and 1.8 mm in thickness) upon which biofilms were formed. Ge disks provided reflective surfaces that allowed the visualization of unstained biofilms using differential interference contrast (DIC) microscopy.

To form biofilms, Ge disks (Mindrum, Rancho Cucamonga, Calif.) in the dual flow cell were conditioned for one hour with sterile 50% human whole saliva. Isolated salivary bacteria, adjusted to approximately $1.0 \times 10^7$ cells/ml in 50% saliva (total, 1.5 ml), were injected into the flow chambers. After two hours of initial adherence of bacteria onto disk surfaces, the flow of culture medium (20% Todd-Hewitt broth) was started at a rate of 0.2 ml/min (Foster et al., 2004). The flow rate employed generated a shear rate of approximately 9.65 $s^{-1}$ on the substrate surface, and is compatible with the fluid flow in the oral cavity (Bakker et al., 2003).

To evaluate the effects of KSL in controlling the development and maturation of oral biofilms, surface adhered cells (after initial colonization) were perfused continuously with KSL-free or KSL-containing media (KSL at 10 or 50 µg/ml). Alternatively, biofilms at different stages of maturation (i.e., 4, or 6 h after inoculation) were pulse-treated using an injection pump at 0.2 ml/min with 50 µg/ml KSL in 20% THB or the control medium for 30 min at 2 hr intervals. Direct comparison of the effects of antimicrobials on the growth of biofilms between treated versus untreated was made in real-time by DIC microscopy.

1.5 Bactericidal Activities of KSL Against Oral Biofilms

In conjunction with the dual flow cell system, a modification of an in vitro plaque model of biofilm formation described by Guggenheim et al. (Guggenheim et al., 2001) was used to determine the effects of tested antimicrobials and other agents on developed oral biofilms (see Appendix I for details). HA disks (Clarkson, south Williamsport, Pa.) were employed as substrates for salivary bacteria to form biofilms.

To determine the inhibitory activity of KSL on developed oral biofilms, disks containing 45 h-old biofilms were transferred to wells containing aqueous KSL (200 µg/ml; 1 ml/well). Following 30 min exposure at 37° C., disks were rinsed with 3×1 ml of saline and transferred to sterile 15 ml polypropylene tubes containing 1 ml PBS. Biofilm cells adherent to surfaces (after treatment) were recovered by sonicating for 2 min at 5 watts with a Microson ultrasonic cell disrupter equipped with a cup horn (Misonix Inc., Farmingdale, N.Y.). Settings including the time interval used in the sonication were predetermined empirically to yield maximal recovery of adherent biofilm cells.

The effect of KSL on disrupted biofilms was assessed by recovering biofilm cells from HA disks (45 h-old biofilms) through sonication as described above. The detached biofilm cells (in sterile $dH_2O$) were mixed with an equal volume of aqueous KSL to obtain a final peptide concentration of 200 µg/ml, and the reaction mixtures incubated at 37° C. for 30 min. The interactions of KSL and suspended biofilm cells were terminated by washing in PBS.

To determine the effect of the surface-active agent (benzalkonium chloride; Sigma, St. Louis, Mo.) in promoting the killing of intact biofilms by KSL, 66 h-old oral biofilms were treated with KSL (200 µg/ml), benzalkonium chloride (0.001%), or a combination of the two agents, followed by viable counts determinations and confocal laser scanning microscopy of treated samples. The benzalkonium chloride dosages were pre-determined empirically to select concentrations of the agent exhibiting minimal bactericidal activity.

Viable counts of biofilm cells derived from treated disks or disrupted biofilms were determined by spiral plating serially diluted samples onto blood agar plates. Distilled water or 0.12% aqueous chlorhexidine digluconate (Sigma) was used as the negative or positive control, respectively. The 45 h-old biofilms were exposed to chlorhexidine for 1 min, and to water for 30 min at 37° C.

2 Results 2.1 Interactions of KSL with Oral Biofilms Formed in Dual Flow Cells

To determine whether KSL has anti-biofilm activity, we examined the effect of various concentrations of KSL on oral biofilm development. Using DIC microscopy we observed the adherence of salivary bacteria to saliva-conditioned Ge surface in the flow chambers 2 h after the inoculation of the flow cell (FIG. 2A, a and d; FIG. 2B, a and c). After the attachment of bacteria to the surface, the flow chambers were perfused continuously with culture medium with or without KSL. In the flow chamber perfused with medium lacking KSL, microcolonies were formed 5 h after the inoculation (FIG. 2A, b) and continued to develop into film-like structures after 8 h (FIG. 2A, c). In contrast, KSL at 50 µg/ml disrupted biofilm development. Bacteria remained attached, but failed to form microcolonies and film-like structure (FIG. 2A, d-f). Further, KSL at 10 µg/ml was partially effective in inhibiting biofilm formation. Microcolonies formed 8 h after inoculation (FIG. 2B, c-d), whereas the untreated adhered salivary bacteria formed film-like structure (FIG. 2B, a-b).

While continuous perfusion of medium containing KSL to the flow chambers prevented the attached salivary bacteria from differentiating into biofilms on conditioned Ge surfaces, we were also interested in determining whether KSL could disrupt the development process by pulsed treatment of biofilm cells at different time points after inoculation. As shown in FIG. 3A (a-c), pulsed treatment (30 min at 0.2 ml/min for every 2 h interval) of biofilm cells 4 h after inoculation with KSL-free medium, did not prevent attached salivary bacteria from developing into biofilms. In contrast, pulsed treatment of biofilm cells 4 h after inoculation with KSL-containing medium (50 µg/ml) inhibited biofilm formation (FIG. 3A, d-f). However, as compared to the controls (FIG. 3B, a-c), pulsed treatment of biofilms 6 h after inoculation with KSL-containing medium failed to inhibit the development of biofilm structures or alter their structures (FIG. 3B, d-f).

2.2 Interactions of KSL with Intact and Disrupted Oral Biofilms

Our flow cell experiments showed that mature oral biofilms were less susceptible to KSL. In contrast, exposure of adhered salivary bacteria or biofilm cells to KSL at earlier stages of development inhibited their further development into mature growing biofilms. In this context, we were interested in determining whether the organized structure of developed oral biofilms contributed to the resistance of mature oral biofilms to KSL using the in vitro plaque assay. As shown in FIG. 4A, there was a small reduction of viable counts (p<0.05) by exposing intact 45-h-old oral biofilms formed on saliva-conditioned HA disks to KSL. A larger reduction of viable counts was observed with intact biofilms treated with 0.12% chlorhexidine. When these biofilms were mechanically disrupted by sonication before KSL treatment, there was a much greater (1.8 log) reduction of viability of KSL-treated cells as compared to $dH_2O$-treated control cells. There was likewise a significant reduction of viability in disrupted biofilms as compared to intact biofilms treated with the same concentration of KSL.

2.3 Interactions of KSL with Intact Oral Biofilms in the Presence of Surface-Active Agent Since the organized structure of biofilms might influence biofilm susceptibility to antimicrobials, we were interested in determining the effect of a surface-active agent, benzalkonium chloride, in promoting the killing of biofilm cells by KSL using the in vitro plaque assay. As shown in FIG. 4B, as compared to water treatment, KSL, in the presence of benzalkonium chloride (0.001%), significantly reduced the viability (over one log reduction) of 66 h-old oral biofilms to a similar extent as that caused by chlorhexidine. KSL (200 µg/ml) or benzalkonium chloride (0.001%) alone had less effect on the viability of these biofilms. These results were confirmed by live/dead staining of treated samples as revealed by confocal microscopy (FIG. 4C)

3. Discussion

The use of a dual flow cell containing removable colonizable surfaces together with isolated salivary bacteria provides an alternative method to examine the effect of antimicrobials on oral biofilm formation. The use of human salivary bacteria as the plaque seeds is particularly relevant as these bacteria are derived from biofilms formed on hard and soft tissues in the oral cavity (Helmerhorst et al., 1999). The system allows nondestructive, direct comparison of biofilm development between the treated and negative control groups.

In this test system, KSL markedly prevented biofilm development as compared to the control. We reasoned that the observed inhibition was probably due to the antimicrobial activity of KSL. We have shown that KSL exert its antimicrobial activity by destabilizing target bacterial membranes (Concannon et al., 2003). In contrast, exposing established oral biofilms (45-h-old biofilms) to KSL did not disrupt their structure or cause any large reductions of viability of biofilm cells. The results indicate that once developed, biofilms were more resistant to KSL. Interestingly, similar properties were observed with lactoferrin, a native antimicrobial component that is abundantly present in surface secretion. Continuous perfusion of lactoferrin at sub-inhibitory concentrations prevents biofilm development by *Pseudomonas aeruginosa*.

However, lactoferrin, like KSL, fails to alter the structure of mature biofilms (Singh et al., 2002).

Several factors influence biofilm susceptibility to antimicrobials (Campanac et al., 2002; Gilbert et al., 1997; Stewart et al., 2004). We hypothesized that the reduced susceptibility of developed oral biofilms to KSL could be due to retarded diffusion or exclusion of our antimicrobial imposed by the three-dimensional biofilm structures and/or the presence of exopolymeric substances. To test this, we disrupted the oral biofilms grown on saliva-coated HA surfaces formed by salivary bacteria and determined the susceptibility of these disrupted biofilm cells to KSL as compared to intact biofilms. We reasoned that the disruption of the biofilm structure would improve the accessibility of the targeted biofilm cells to our antimicrobial agent. Indeed, the disruption procedure greatly enhanced the susceptibility of biofilm cells from disrupted as compared to intact oral biofilms, suggesting that the organized structure of biofilms might play a role in influencing the susceptibility of intact biofilms to antimicrobials. However, we are uncertain whether the reduced susceptibility observed with intact biofilms is also attributable to the exopolymers that might be associated with the biofilm cells. Further, sub-bactericidal concentrations of benzalkonium chloride, a known cationic surface-active agent (Baker et al., 1978), significantly promoted biofilm susceptibility to KSL. Though we are not clear about the underlying mechanisms, one possible explanation is that the presence of sub-inhibitory concentrations of benzalkonium chloride might facilitate the accessibility of biofilm cells residing in intact oral biofilms to KSL by influencing biofilm structures. Alternatively, the cationic agent benzalkonium chloride could provide a synergistic effect on the bactericidal activity of KSL in killing salivary bacteria.

The findings that KSL prevented the development of oral biofilms raise the possibility that KSL could be a valuable adjunct to toothpastes for preventing plaque-mediated dental diseases. This is particularly relevant since KSL was effective in killing disrupted oral biofilm cells. This disruption could be generated by mechanical brushing and/or flossing during oral hygiene procedures.

C. Newly Developed Antimicrobial Peptides

KSL-W, an L-tryptophan analog of KSL wherein the L-lysine residue at the number six position is replaced with L-tryptophan. The sequence is: $NH_2$-Lys-Lys-Val-Val-Phe-Trp-Val-Lys-Phe-Lys-$CONH_2$ (SEQ ID NO 2).

KSL-M, an analog of KSL wherein the L-lysine residue at the number six position is replaced with an α-methylated L-lysine. The sequence is: $NH_2$-Lys-Lys-Val-Val-Phe-Lys(me)-Val-Lys-Phe-Lys-$CONH_2$ (SEQ ID NO 3).

H1-2, a double helical hybrid molecule consists of KSL-W and an analog of the N-terminal sequence derived from a salivary protein, statherin. The sequence is: $NH_2$-Asp-Asp-Asp-Glu-Glu-Lys-Phe-Leu-Arg-Arg-Ile-Gly-Arg-Tyr-Gly-Lys-Lys-Val-Val-Phe-Trp-Val-Lys-Phe-Lys-$CONH_2$ (SEQ ID NO 4).

1. Susceptibility Tests of Drug-Resistant Pathogens to Newly Developed Antimicrobial Peptides.

As shown in the table below, many drug-resistant pathogens including multidrug-resistant *Acinetobacter baumannii* (clinical isolates) were susceptible to the bactericidal activity of the newly developed antimicrobial peptides. In general, the newly developed (i.e., second generation) antimicrobial peptides, which included KSL-W and H1-2, are more potent than the parent antimicrobial peptide, KSL. This is shown by their lower MIC and MBC against a number of antibiotic-resistant bacteria including methicillin-resistant *Staphylococcus aureus*, vancomycin-resistant Enterococci, and multidrug-resistant *Acinetobacter baumannii*. Many of these resistant strains are involved in nosocomial infections, which affect the immunocompromised and the elderly individuals with weakened defenses. The tests were done in a broth microdilution assay as described in our earlier publication (Concannon et al., 2003).

| | KSL | | KSL-W | | KSL-M | | H1-2 | |
|---|---|---|---|---|---|---|---|---|
| Organism | MIC (µg/ml) | MBC (µg/ml) | MIC (µg/ml) | MBC (µg/ml) | MIC (µg/ml) | MBC (µg/ml) | MIC (µg/ml) | MBC (µg/ml) |
| *A. baumannii* ATCC #19606 | 100 | 200 | >25 < 50 | 100 | ND | ND | 12.5 | 25 |
| *A. baumannii* WRAMC #2 | >50 < 100 | 100 | 25 | 100 | >100 < 200 | 200 | 25 | 200 |
| *A. baumannii* WRAMC #4 | 12.5 | 25 | >12.5 < 25 | 25 | 25 | 50 | 25 | 50 |
| *A. baumannii* WRAMC #5 | >25 < 50 | 50 | 12.5 | 25 | >25 < 50 | 50 | >12.5 < 25 | 25 |
| *A. baumannii* WRAMC #8 | >50 < 100 | 100 | >12.5 < 25 | 25 | >200 | >200 | >12.5 < 25 | 25 |
| *A. baumannii* WRAMC #11 | 100 | 200 | >12.5 < 25 | 25 | >50 < 100 | 100 | 25 | 50 |
| *A. baumannii* WRAMC #13 | 50 | 200 | >12.5 < 25 | 50 | >50 < 100 | 200 | >12.5 < 25 | 50 |

-continued

| Organism | KSL MIC (μg/ml) | KSL MBC (μg/ml) | KSL-W MIC (μg/ml) | KSL-W MBC (μg/ml) | KSL-M MIC (μg/ml) | KSL-M MBC (μg/ml) | H1-2 MIC (μg/ml) | H1-2 MBC (μg/ml) |
|---|---|---|---|---|---|---|---|---|
| A. baumannii WRAMC #14 | >50 < 100 | 100 | 25 | 50 | >100 < 200 | 200 | >6.25 < 12.5 | 50 |
| A. baumannii WRAMC #15 | 100 | >200 | >25 < 50 | 50 | ND | ND | 25 | 50 |
| A. baumannii WRAMC #16 | >12.5 < 25 | 25 | >12.5 < 25 | 50 | 50 | 100 | 12.5 | 25 |
| A. baumannii WRAMC #17 | >50 < 100 | 100 | >12.5 < 25 | 25 | 100 | 200 | 25 | 100 |
| A. baumannii WRAMC #18 | 50 | 200 | 12.5 | 25 | >50 < 100 | 100 | >12.5 < 25 | 25 |
| A. baumannii WRAMC #19 | >25 < 50 | 50 | 50 | 100 | ND | ND | >50 < 100 | 200 |
| MRSA ATCC #33591 | 200 | >200 | 100 | 200 | >200 | >200 | 3.125 | 12.5 |
| MRSA ATCC #43300 | 100 | 200 | 25 | 50 | >200 | >200 | 3.125 | 12.5 |
| MRSA WRAMC #1 | >200 | >200 | >50 < 100 | 100 | >200 | >200 | >3.125 < 6.25 | 25 |
| MRSA WRAMC #9 | >200 | >200 | 200 | >200 | >200 | >200 | >1.56 < 3.125 | 3.125 |
| MRSA WRAMC #10 | >200 | >200 | >100 < 200 | 200 | >200 | >200 | 1.56 | 25 |
| MRSA WRAMC #12 | >200 | >200 | 200 | >200 | >200 | >200 | 3.125 | 6.25 |
| VRE ATCC #51299 | >200 | >200 | 100 | 200 | ND | ND | 12.5 (25) | 50 |
| VRE WRAMC #3 | >200 | >200 | 100 | 200 | ND | ND | 6.25 | 25 |
| VRE WRAMC #6 | >25 < 50 | 100 | 12.5 | 100 | ND | ND | <1.56 | 6.25 |
| VRE WRAMC #7 | >50 < 100 | 100 | >6.25 < 12.5 | 25 | ND | ND | <1.56 | 0 |

MIC, minimum inhibitory concentrations
MBC, minimum bactericidal concentrations
MRSA, methicillin-resistant *Staphylococcus aureus*
VRE, vancomycin-resistant *Enterococci*

2. Synergistic interactions of cationic surface of cationic surface-activating agents (benzalkonium chloride and cetyl pyridinium chloride) and our antimicrobial peptides (parent antimicrobial peptide, KSL and second generation antimicrobial peptide, KSL-W) as determined by a checkerboard plate assay.

A modified checkerboard assay of combined antimicrobial activity described by Singh et al. (Singh et al., 2000) was used to determine the interactions of the antimicrobial peptides (KSL and KSL-W) and surface-activating agents [benzalkonium chloride (Bzl) and cetyl pyridinium chloride (CPC)] on the killing of salivary bacteria. Two-fold serial dilutions of the peptides (started at 800 μg/ml) and surface-activating agents (started at 0.003% or 30 fig/nil) were mixed together in a microtiter plate. Each row and column contained a fixed amount of one agent and increasing amounts of the second agent. Each plate also contained a row and column in which a serial dilution of each agent was present alone. An additional column containing just bacteria was used as a control. Salivary bacteria ($1\times10^6$ cells/ml) were added to each well, and turbidity was measured after overnight incubation, at 37° C. in a $CO_2$ incubator at 600 nm by using an ELISA reader (Titertek Multiskan MCC/340). Clear (non-turbid) well indicated growth inhibition.

The degree of synergy between the two agents is expressed in terms of the fractional inhibitory concentration (FIC). The FIC is defined as the Minimum Inhibitory Concentration (MIC) of test agents used in combination divided by the MIC of the agent acting alone (Hall et al., 1983). The FIC index, which defines the nature of the interaction, is the sum of the individual FIC values of two agents that has the most effective combination in antimicrobial activity. Antimicrobial agents with additive interactions have a FIC index of ~1, whereas combinations with an FIC index <1 indicate synergistic interactions. In contrast, combinations with an FIC index >1 are antagonistic (Hall et al., 1983; Singh et al., 2000). The calculated FIC index of KSL and Bzl combinations was 0.3125, suggesting that this surface-active agent provides a synergistic effect on the bactericidal activity of KSL. Further, the results of the checkerboard assay can be represented by plotting the FIC values of KSL and Bzl as an isobologram (Hall et al., 1983; Singh et al., 2000). As indicated in FIG. 12, the isobol appears to be concave, indicating that these two agents have synergistic antimicrobial activity. A convex isobol suggests antagonistic interactions of the two agents. The results from the interactions of KSL or KSL-W with CPC as shown in FIGS. 13 and 14, respectively, were also indicative of synergy between the test agents.

3. Effects of the Combined Use of Surface-Activating Agents and Antimicrobial Peptides (Parent Antimicrobial Peptide, KSL and Second Generation Antimicrobial Peptide, KSL-W) for Controlling Biofilm Growth.

The impact of surface-activating agents on the ability of the antimicrobial peptides to control biofilm growth was determined by viability studies using an in vitro plaque assay and confocal laser scanning microscopy.

(a) In Vitro Plaque Assay

In this assay, HA disks (Clarkson Chromatography Products, Inc., South Williamsport, Pa.) were used as surfaces on which plaque formation can occur. Before use, sterile HA disks were conditioned in the wells of a 24-well microtiter plate (Becton Dickinson, Franklin Lakes, N.J.) containing 50% sterile saliva by incubating at room temperature for a minimum of two hours on a rotating platform at 95 rpm. The saliva was removed and each well inoculated with isolated salivary bacteria at a bacterial cell concentration of $1.0 \times 10^7$ cells/ml in sterile 50% whole saliva. After two hours of incubation (with rotation) at 37° C. to allow the bacteria to adhere to surfaces, unattached bacteria were removed and replaced with supplemented saliva-based medium. The plates were incubated with rotation at 37° C. for 45 h (with medium replaced three times), or 66 h (with medium replaced five times) in a $CO_2$ incubator prior to treatments, and the recovery of biofilm cells from treated or untreated disks.

As shown in these assays (FIGS. 15, 16, and 17) KSL combining with Bzl or KSL-W in combination with Bzl or CPC effectively caused significant reductions of the viability of biofilm cells derived from treated oral biofilms. In these studies, KSL or KSL-W was used at 200 µg/ml, whereas Bzl and CPC were used at 0.001% and 0.0025%, respectively. The exposure time for the interactions of biofilms with distilled water, KSL, KSL-W, Bzl, or CPC was 30 min at 37° C. Following the treatment, disks were rinsed with 3×1 ml of saline and transferred to sterile 15 ml polypropylene tubes containing 1 ml phosphate-buffered saline. Biofilm cells adherent to surfaces (after treatment) were recovered by sonicating for 2 min at 5 watts with a Microson ultrasonic cell disrupter equipped with a cup horn (Misonix Inc., Farmingdale, N.Y.). Settings including the time interval used in the sonication were pre-determined empirically to yield maximal recovery of adherent biofilm cells. Viable counts of biofilms derived from treated disks were determined by spiral plating (Microbiological International) serially diluted samples onto blood agar plates.

4. Adherence Inhibition of Tritiated *Actinomyces* Naeslundii to Saliva-Coated Hydroxapatite (HA) Disks by KSL-W.

In these studies, saliva-coated HA disks pre-treated with salivary proteins, KSL-W (1 mg/ml), or chlorhexidine (1 mg/ml), were used as colonizable surfaces to test the adherence of tritiated *A. naeslundii*, an early colonizer that is involved in dental plaque formation. In these experiments, labeled *A. naeslundii* (1×10' cells per ml) were incubated for 2 h with HA disks that were pre-treated with different agents. As show in FIG. 18, HA disks pretreated with KSL-W showed a great reduction in the number of bacteria that attached during the 2 hour incubation at 37° C. The results suggest that our antimicrobial peptides exhibit antiadherence activity that prevents bacteria from colonizing surfaces.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

The invention claimed is:

1. An antibacterial composition, comprising: an antimicrobial decapeptide KSL-W (SEQ ID NO:2) and a cationic surface active agent.

2. The composition according to claim 1, wherein the composition is in the form of aqueous mouth rinse or chewing gum.

3. The composition according to claim 1, wherein the surface active agent is selected from the group consisting of benzalkonium chloride, benzyl chloride, and cetylpyridinium chloride (CPC).

4. A method of treating mature oral biofilms, comprising contacting a composition comprising the antimicrobial decapeptide KSL-W (SEQ ID NO: 2) and a cationic surface active agent with mature oral biofilm in the mouth of a user, wherein said composition is in the form of an aqueous mouth rinse or chewing gum.

5. The method according to claim 4, wherein the cationic surface active agent is selected from the group consisting of benzalkonium chloride, benzyl chloride, and cetylpyridinium chloride (CPC).

6. A method of treating mature oral biofilms, comprising: mechanically disrupting the mature oral biofilm; and contacting a composition comprising the antimicrobial decapeptide KSL-W (SEQ ID NO: 2) with the disrupted mature oral biofilm in the mouth of a user.

7. The method according to claim 6, wherein the composition is in the form of toothpaste.

* * * * *